US012616731B2

(12) United States Patent   (10) Patent No.: US 12,616,731 B2

Ramanathan et al.   (45) Date of Patent: May 5, 2026

(54) PROCESS FOR ENHANCING ORGANOLEPTIC PROPERTIES OF NATURAL PRODUCTS AND NATRACEUTICALS THEREOF

(71) Applicant: DiaBliss Consumer Products Pvt Ltd, Chennai (IN)

(72) Inventors: Vr. Ramanathan, Chennai (IN); Siva Vallabhaneni, Chennai (IN); V. Rajalakshmi, Chennai (IN)

(73) Assignee: DiaBliss Consumer Products Pvt Ltd, Chennai (IN)

( * ) Notice: Subject to any disclaimer, the term of this patent is extended or adjusted under 35 U.S.C. 154(b) by 509 days.

(21) Appl. No.: 18/246,552

(22) PCT Filed: Sep. 22, 2021

(86) PCT No.: PCT/IN2021/050933

§ 371 (c)(1),
(2) Date: Mar. 24, 2023

(87) PCT Pub. No.: WO2022/064522

PCT Pub. Date: Mar. 31, 2022

(65) Prior Publication Data

US 2023/0364177 A1     Nov. 16, 2023

(30) Foreign Application Priority Data

Sep. 25, 2020   (IN) .............................. 202041041780

(51) Int. Cl.
*A61K 36/9066*      (2006.01)
*A23L 5/10*         (2016.01)
(Continued)

(52) U.S. Cl.
CPC ............ *A61K 36/9066* (2013.01); *A23L 5/11* (2016.08); *A23L 27/10* (2016.08); *A61K 36/185* (2013.01);
(Continued)

(58) Field of Classification Search
CPC .. A61K 36/9066; A61K 36/185; A61K 36/23; A61K 36/235; A61K 36/48; A61K 36/54; A61K 36/61; A61K 36/67; A61K 36/71; A61K 36/79; A61K 36/9068; A61K 2236/15; A61K 2236/331; A61K 2236/53;
(Continued)

(56) References Cited

FOREIGN PATENT DOCUMENTS

WO        03074145 A1      9/2003
WO        2001007534 A1    2/2021

OTHER PUBLICATIONS

Handground, How to Make Chemex Coffee, 2017, pp. 1-18. (Year: 2017).*

(Continued)

*Primary Examiner* — Trevor Love
(74) *Attorney, Agent, or Firm* — Kevin J Fournier Intellectual Property Legal Services Ltd.; Kevin J Fournier

(57) ABSTRACT

A method for increasing functional and organoleptic properties of compositions having elements of biological origin more particularly herbal formulations is disclosed. Nutraceutical formulations for diabetes management and fortification of pulses and grains to lower oil absorption during frying are also disclosed. These foods are effective for weight management.

11 Claims, 4 Drawing Sheets

Figure 1:
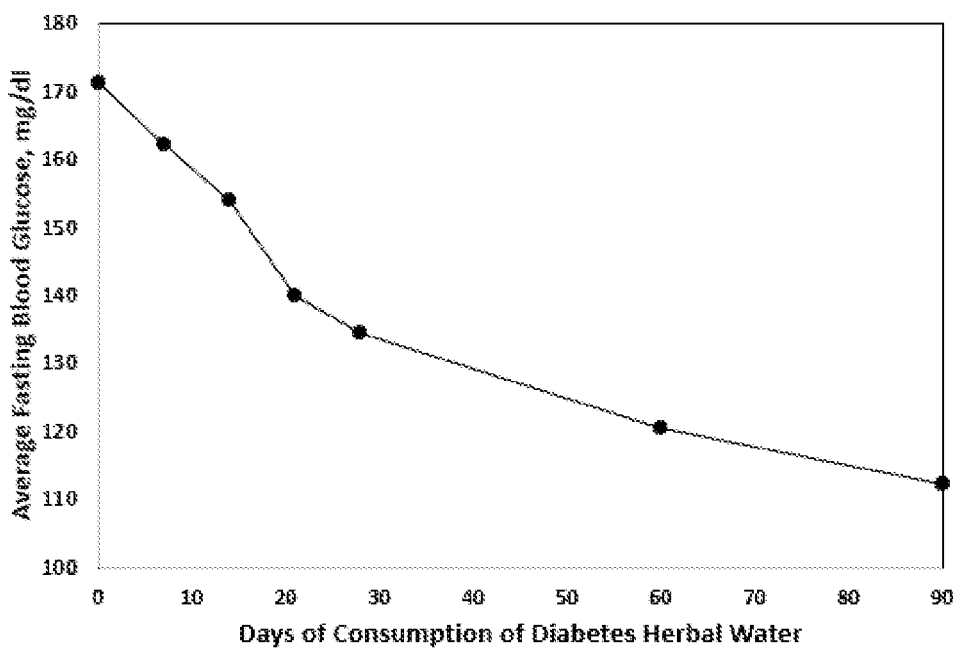

(51) Int. Cl.

| | |
|---|---|
| *A23L 27/10* | (2016.01) |
| *A61K 36/185* | (2006.01) |
| *A61K 36/23* | (2006.01) |
| *A61K 36/235* | (2006.01) |
| *A61K 36/48* | (2006.01) |
| *A61K 36/54* | (2006.01) |
| *A61K 36/61* | (2006.01) |
| *A61K 36/67* | (2006.01) |
| *A61K 36/71* | (2006.01) |
| *A61K 36/79* | (2006.01) |
| *A61K 36/9068* | (2006.01) |
| *A61P 3/10* | (2006.01) |
| *B01D 1/22* | (2006.01) |
| *B01D 3/10* | (2006.01) |
| *B01D 5/00* | (2006.01) |
| *B01D 15/36* | (2006.01) |

(52) U.S. Cl.
CPC ............ *A61K 36/23* (2013.01); *A61K 36/235* (2013.01); *A61K 36/48* (2013.01); *A61K 36/54* (2013.01); *A61K 36/61* (2013.01); *A61K 36/67* (2013.01); *A61K 36/71* (2013.01); *A61K 36/79* (2013.01); *A61K 36/9068* (2013.01); *A61P 3/10* (2018.01); *B01D 1/222* (2013.01); *B01D 3/10* (2013.01); *B01D 5/0003* (2013.01); *B01D 15/363* (2013.01); *A61K 2236/15* (2013.01); *A61K 2236/331* (2013.01); *A61K 2236/53* (2013.01); *A61K 2236/55* (2013.01)

(58) Field of Classification Search
CPC ....... A61K 2236/55; A23L 5/11; A23L 27/10; B01D 1/222; B01D 3/10; B01D 5/0003; B01D 15/363
See application file for complete search history.

(56) References Cited

OTHER PUBLICATIONS

WO, International Search Report; PCT/IN2021/050933, Jan. 20, 2022 (17 pages).

Mccloud, High throughput extraction of plant, marine and fungal specimens for preservation of biologically active molecules, Molecules, Jun. 24, 2010, p. 4526-63, vol. 15 Issue 7. DOI: 10.3390/molecules15074526.

Suryaningsih et al., Bioactive Content and Antioxidant Activity of Albedo Pomelo (*Citrus grandis*, C. Maxima) Extract Using a Method of 2,2-Dhipenil-1-Picrylhydrazyl (DPPH) in Various Types of Extraction Solvent, Asian Jr. of Microbiol. Biotech. Env. Sc., Feb. 12, 2019, p. 846-850, vol. 21 Issue 4.

Sonar el al., Extraction of type II antidiabetic compound corosolic acid from Lagerstroemia speciosa by batch extraction and three phase partitioning, Biocatalysis and Agricultural Biotechnology, Aug. 6, 2020, p. 101694, vol. 27 Issue 1. https://doi.org/10.1016/j.bcab.2020.101694.

Qiu et al., Agitated thin-film drying of foods, Drying Technology, Jan. 10, 2018, p. 735-744, vol. 37 Issue 6. https://doi.org/10.1080/07373937.2018.1458037.

Aissaoui et al, Hypoglycemic and hypolipidemic effects of *Coriandrum sativum* L. in Meriones shawi rats, Dec. 15, 2010, p. 652-661, vol. 137 Issue 1. https://doi.org/10.1016/j.jep.2011.06.019.

Patil et al., Insulin Secretagogue, Alpha-glucosidase and Antioxidant Activity of Some Selected Spices in Streptozotocin-induced Diabetic Rats, Plant Foods for Human Nutrition, Mar. 25, 2011, p. 85-90, vol. 66 Issue 1. DOI: 10.1007/s11130-011-0215-7.

Khaliq et al., Recent Progress for the Utilization of Curcuma longa, Piper nigrum and Phoenix dactylifera Seeds against Type 2 Diabetes, West Indian Medical Journal, Mar. 4, 2016, p. 527-32, vol. 64 Issue 5. DOI: 10.7727/wimj.2016.176.

Jagtap et al., Antihyperglycemic activity and inhibition of advanced glycation end product formation by Cuminum cyminum in streptozotocin induced diabetic rats, Food and Chemical Toxicology, May 6, 2010, p. 2030-2036, vol. 48 Issues 8-9. https://doi.org/10.1016/j.fct.2010.04.048.

Najmi et al., Therapeutic effect of Nigella sativa in patients of poor glycemic control, Asian Journal of Pharmaceutical and Clinical Research, Jan. 2012, p. 224-228, vol. 5.

Gupta et al., Effect of Trigonella foenum-graecum (fenugreek) seeds on glycaemic control and insulin resistance in type 2 diabetes mellitus: a double blind placebo controlled study, J Assoc Physicians India, Nov. 2001, p. 1057-61, vol. 49.

* cited by examiner

Control Sample (No Herbal Treatment)      Herbal Treatment of foxtail millet & Rice @ 60 ml/kg

PROCESS FOR ENHANCING ORGANOLEPTIC PROPERTIES OF NATURAL PRODUCTS AND NATRACEUTICALS THEREOF

CROSS-REFERENCE TO RELATED APPLICATIONS

The present invention is filed under 35 U.S.C. § 371 as the U.S. national phase of International Patent Application No. PCT/IN2021/050933, filed Sep. 22, 2021, which designated the United States and which claims the benefit of India patent application Ser. No. 202041041780 filed Sep. 25, 2020, which is hereby incorporated in its entirety including all tables, figures, and claims.

FIELD OF THE INVENTION

The subject matter described herein, in general, relates to a method for increasing functional and organoleptic properties of compositions having elements of biological origin more particularly herbal formulations. It also discloses nutraceutical formulations for diabetes management and fortification of pulses and grains to lower oil absorption during frying, thus also making these foods effective for weight management.

BACKGROUND OF THE INVENTION

Diabetes mellitus is a chronic disease which is an incurable ailment and a better management is the only way for a better life. In Diabetes mellitus an increased level of glucose in the blood causes damage to many of the body's systems, particularly the blood vessels and the nerves. Both, Type 1 diabetes and Type 2 diabetes mellitus are complex diseases caused by mutations in more than one gene either inherited or a result of any environmental factor(s). Treatment of type 1 diabetes is based on daily administration of insulin. Type 2 diabetes or non-insulin dependent diabetes mellitus (NIDDM) is much more common and accounts for around 90% of all diabetes cases worldwide. It develops mostly in the adult age, but lately it has been also noted in young people, even in adolescents. Diabetes type 2 is strongly familial, but environmental factors play also an important role in the development of the disease. Healthy diet, practice of physical exercise and avoidance of overweight may prevent the disease and/or control its progress. People with type 2 diabetes require oral agents for satisfactory blood glucose control, but about one third needs insulin for reducing their blood glucose levels.

Several complications are associated with diabetes including: (i) retinal and ophthalmic manifestations or dysfunctions such as retinopathy (ii) neuropathy consisting of peripheral nerves damages, feet pains, feet low pulse and edemas, blood circulation dysfunction, walking difficulties and legs wounds (iii) liver dysfunction consisting of hypercholesterolemia, proteinuria and hyperlipidemia, (iv) renal dysfunction—sometimes defined as Nephrotic syndrome consisting of lipiduria, hypercholesterolemia, hypoalbuminemia, edema, proteinuria, hyperlipidemia or microalbuminemia, prostate enlargement, ketones in urine, hypertension, and (vi) cardiovascular disease ranging from coronary artery disease to stroke or renal vascular disease, consisting of arterioscleroses, heart disease, valvular heart disease, disease of the heart muscle, arrythmias and noncoronary cardiovascular disease.

People with diabetes are more prone to infection. They can also develop neuropathy (damaged nerves) or peripheral vascular disease (blocked arteries) of the legs and either can lead to foot ulceration. Infection and foot ulceration, alone or in combination, often lead to amputation. Neuropathy and peripheral vascular disease can also cause distressing pain in the lower limbs.

Diabetes-related complications are a leading cause of death. Controlling blood sugar levels will help ensure that diabetes is managed successfully and reduce the risk of short and long-term complications that diabetes can cause like diabetic retinopathy, heart disease, which accounts for about 50% of all deaths among people with diabetes in industrialized countries, kidney failure, diabetic neuropathy, the most common complication of diabetes, that may lead to sensory loss and damage to the limbs, and to impotence in diabetic men and diabetic foot disease, one of the most common and costly complications of diabetes, that results from both vascular and neurological disease processes that often lead to ulceration and subsequent limb (mainly lower limb) amputation. Thus, in addition to the medicines and or insulin administration diabetes management is an essential aspect for avoiding and/or delaying short and long-term complications, managing dependence on medicines and for improving the quality of life. Nutraceuticals are emerging as one of the most promising management tools for diabetes. Naturally derived nutraceuticals from food ingredients provide functional property enhancements to foods in a healthy and safe manner Thus, there is a constant need for nutraceuticals to deal with various aspects of diabetes treatment and management like low fat absorbing foods to lower calorie intake for weight management benefits and provide safe and healthy alternatives.

The current invention relates to a process of enhancing functional and organoleptic properties of natural products and nutraceuticals thereof. More specifically they involve use of many herbs and spices. These herbs and spices, while possessing many health and wellness properties, provide many properties in food preparations such as color, flavor, aroma and texture. In order to provide the necessary benefits, they have to be consumed in large quantities in their native form.

For example, a clinical study titled, "Effectiveness of Fenugreek for Lowering Hemoglobin (HbA1c) in Patients with Self-Management of Type 2 Diabetes: A Randomized Controlled Trial" by Ansari R, Ansari S, published in Intech Open, www.intechopen.com, September 2011, 100 g of Fenugreek was consumed by participants in clinical trial to lower long term blood sugar values as measured by glyacated Hemoglobin or HbA1c.

Similar studies were conducted with other herbs, spices or foods where 10 g of Black Jamun (ref: Sidana S, Singh V B, Meena B L, Beniwal S, Singh K, Kumar D, et al. Effect of *Syzygium cumini* (jamun) seed powder on glycemic control: A double-blind randomized controlled trial. J Med Soc 2017; 31:185-9.) was consumed by subjects or 30 g per day of Amla was consumed (Santhi Sri K V, Jalaja Kumari D, Sivanarayana G, Effect of Amla, an approach towards the control of Diabetes mellitus, Int.J.Curr.Microbiol.App.Sci (2013) 2(9): 103-108). Consuming such large quantities of these foods in their native forms daily for extended periods of time become difficult and impractical.

The current invention of extracting the necessary ingredients into a water format and a relatively pleasing taste allows the required efficacy or functionality to be delivered in an easily consumable format.

Thus, the major challenge for developing the nutraceuticals with an aim to incorporate them into the daily lifestyle as daily consumable item was to enhance their organoleptic properties in addition to functional properties. As the herbal formulations which though might be effective but if not palatable would not be accepted. As nutraceutical products from the current invention are water based with excellent organoleptic properties, it allows daily consumption of required portion of nutraceuticals and also allows fortification of beverages, dairy products or meal replacement shakes to deliver daily requirement into daily lifestyles.

SUMMARY

It is an object of the present subject matter to provide for a method for enhancing functional and organoleptic properties of herbal compositions.

In one of the embodiments of the present invention it discloses method for manufacturing a formulation of natural products comprising herbs, plants and/or spices and/or part thereof with enhanced functional and organoleptic properties comprising the steps of:

a. Selection of herbs and/or spices b. Grinding of herbs and/or spices under controlled condition(s) to a desired particle size c. Mixing of the herbs of step b.

d. The resultant powder of step c is homogenized with water into a slurry

The herbs and/or spices used in the method are selected with the moisture content, when dried 5% to 25%, and when fresh with 80% to 85%. Further, the grinding performed in the method is preferably done by hammer mill or commercial food shredder pulveriser. The hammer mill is operated preferably between 1500 RPM-2000 RPM and more preferably between 1600 RPM-1800 RPM. The desired particle size of the constituents achieved by the grinding process preferably ranges between 30 microns-300 microns for manufacturing a formulation with desired properties of the present invention. The method as discussed above, the step c for manufacturing a slurry formulation and/or formulation in a filtrate further comprises the following steps:

a. The herbal formulation of step (c), is dissolved in desired quantity of water.

b. The mixture of step (a) is kept in a jacketed stirred tank for about 4-16 hours at a temperature of 25 deg C. to 60 deg C.

c. The slurry of step (b) is filtered under pressure d. Distillation of the filtrate of step c e. Distillation of the slurry of step c f. Organoleptic herbal concentrate was collected g. The filtrate of step (d) optionally be filtered In yet another embodiment the method of the present invention, in the step c for the manufacturing a slurry formulation and/or formulation in a filtrate alternatively may further comprises the following steps:

e. The herbal formulation obtained by the above method in step (c), is dissolved in desired quantity of water.

f. The mixture of step (a) is kept in a jacketed stirred tank for about 4-16 hours at a temperature of 25 deg C. to 60 deg C.

g. The slurry of step (b) is filtered under pressure h. Contacting the filtrate with activated carbon with a BET surface area of 500-1,700 sq metres per gram for a period of 30-60 minutes at a temperature of 35-65 deg C.

i. Herbal filtrate after treatment with activated carbon is collected after removal of color and taste causing compounds In yet another embodiment the method of the present invention, in the step c for the manufacturing a slurry formulation and/or formulation in a filtrate alternatively may further comprises the following steps:

j. The herbal formulation obtained by the above method of step (c), is dissolved in desired quantity of water.

k. The mixture of step (a) is kept in a jacketed stirred tank for about 4-16 hours at a temperature of 25 deg C. to 60 deg C.

l. The slurry of step (b) is filtered under pressure m. Contacting the filtrate in an ion-exchange column containing anionic polymers such as microporous grade polystyrenic strong base type I anion exchanger having quarternary ammonium functional groups, non-ionic polydivinyl benzene adsorbant resins, styrene matrix and acrylic matrix resins with BET surface area of 500-1,200 sq metres per gram n. Herbal filtrate after treatment with ion exchange column is collected after removal of color and taste causing compounds The method as disclosed in the present invention, the distillation of step (c) was performed in vacuum between 0.01 torr to 300 torr, preferable range between 0.05 to 100 torr. The temperature of step (b) could preferably between 25 to 55 deg C. Further, the filtration of step (c) is preferably carried out by plate and frame or membrane press operating at pressures ranging between 2 to 15 bars. The distillation of step (d) is preferably carried out in a rotary evaporator. Said evaporator is immersed in the heated water bath or water/glycol bath and is preferably rotated at 40-70 rpm. The evaporator is further fitted with the condenser cooled with chilled water or water/glycol mixture. The condenser is further connected with a vacuum pump operating at vacuum levels between 0.05 torr to 100 torr. The residence time for the batch preferably ranges from 3 hours to 12 hours. The distillation of slurry is preferably done by glass batch distillation and which is preferably provided with a impeller. The glass batch distillation is preferably immersed in a heater oil batch. Further, the batch distillation is condensed preferably in a shell and tube condenser. Said condenser is preferably chilled with water or water/glycol mixture to condense the vapor. The distillation/condenser unit(s) is operated at vacuum levels between 0.01 torr to 100 torr. The residence time for the batch preferably ranges from 3 hours to 12 hours.

The distillation step (d) can also be carried out in other types of distillation equipment such as wet film evaporator (WFE) or agitated thin film evaporator (ATFE) or agitated thin film distillation (ATFD) device.

Further, the method as disclose in the present invention above, the slurry of step b may optionally be charged to an Agitated Thin Film Evaporator (ATFE) or Wet Film Evaporator (WFE). The system is preferably operated under vacuum ranging from 0.01 torr to 100 torr and the residence time in the ATFE unit preferably varies from 1 second to 60 seconds. The range of overall herbal extract recoveries from batch distillation to ATFE ranges from 40% to 95%.

The distillation step (d) can also be carried out in other types of distillation equipment such as rotary evaporator and wet film evaporator (WFE).

Yet another object of the present subject matter is to provide for nutraceutical formulations for diabetes management and low-fat absorbing foods for weight management benefits. A primary objective of the current invention is to produce nutraceutical supplements in a highly efficacious and effective form.

A herbal Formulation for the treatment and management of diabetes comprising essentially of a therapeutically effective amount of *Coriandrum sativum* L., *Illicium verum, Curcuma longa, Cuminum cyminum, Nigella sativa, Trigonella foenum-graecum, Piper nigrum, Syzygium aromaticum, Zingiber officinale, Phyllanthus emblica, Syzygium cumini, Cinnamomum verum, Senna alexandrina, Psidium guajava, Piper Nigrum, Trachyspermum ammi, Foeniculum vulgare*. The aforesaid herbal formulation broadly comprises of the herbal constituents in the range of *Coriandrum sativum* L. 0.0-10.0%, *Illicium verum* 0.0%-5.0%, *Curcuma longa* 1.0%-15.0%, *Cuminum cyminum* 0%-20.0%, *Nigella sativa* 0.0%-20.0%, *Trigonella foenum-graecum* 2.0%-20.0%, *Piper nigrum* 5.0%-20.0%, *Syzygium aromaticum* 1.0%-20.0%, *Zingiber officinale* 1.0%-20.0%, *Phyllanthus emblica* 3.0%-35.0%, *Syzygium cumini* 5%-60.0%, *Cinnamomum verum* 1.0%-20.0%, *Senna alexandrina* 0.0%-50.0%, *Psidium guajava* 0.0%. 7.5%, *Piper Nigrum* 0.0%-5.0%, *Trachyspermum ammi* 0.0%-7.5% and *Foeniculum vulgare* 0.0%-5.0%.

The herbal formulation of the present invention could be manufactured using parts of the plants used for preparing the extracts are *Coriandrum sativum* L. Seeds, *Illicium verum* Fruit, *Curcuma longa* Root., *Cuminum cyminum* Seeds, *Nigella sativa* Seeds., *Trigonella foenum-graecum* Seeds., *Piper nigrum* Fruit, *Syzygium aromaticum* Flower Buds, *Zingiber officinale* Root., *Phyllanthus emblica* Fruit., *Syzygium cumini* Fruit & Seed, *Cinnamomum verum* Bark, *Senna alexandrina* Leaves, Flower and Stem, *Psidium guajava* Leaves & Fruit, *Piper Nigrum* Fruit, *Trachyspermum ammi* Fruit, *Foeniculum vulgare* Fruit As yet another embodiment the herbal formulation constituents are present in the range of *Syzygium cumini* 35%, *Phyllanthus emblica* 12.0%, *Piper nigrum* 10.0%, *Trigonella foenum-graecum* 10.0%, *Curcuma longa* 10.0%, *Cinnamomum verum* 7.5%, *Syzygium aromaticum* 7.5% and *Zingiber officinale* 7.5%.

As another embodiment the herbal formulation of the present invention comprises of the herbal constituents present in the range of *Coriandrum sativum* L.1.0%, *Illicium verum* 1.0%, *Curcuma longa* 4.0%, *Cuminum cyminum* 5.0%, *Nigella sativa* 5.0%, *Trigonella foenum-graecum* 5.0%, *Piper nigrum* 6.0%, *Syzygium aromaticum* 3.5%, *Zingiber officinale* 6.0%, *Phyllanthus emblica* 7.0%, *Syzygium cumini* 15.0%, *Cinnamomum verum* 7.5%, *Senna alexandrina* 28.0%, *Psidium guajava* 2.5%, *Piper Nigrum* 1.5%, *Trachyspermum ammi* 2.0% and *Foeniculum vulgare* 2.5%.

In yet another embodiment the present invention discloses use of herbal water condensate as direct consumption or admixed with water, in fortified beverages, dairy applications and meal replacement shakes for management of blood glucose, improvement in HbA1c, FBG, PPBG, lipids levels, etc. for the better treatment and management of diabetes more particularly diabetes mellitus, heart related ailments. Further, fortification of grains and legumes with water based herbal water condensate disclosed in current invention reduces oil consumed during deep fat frying which lowers the calorific intake and helps in weight management, reduction in heart ailments from high lipids levels and the like.

BRIEF DESCRIPTION OF ACCOMPANYING DRAWINGS

The foregoing and further objects, features and advantages of the present subject matter will become apparent from the following description of exemplary embodiments with reference to the accompanying drawings.

Figure 4:
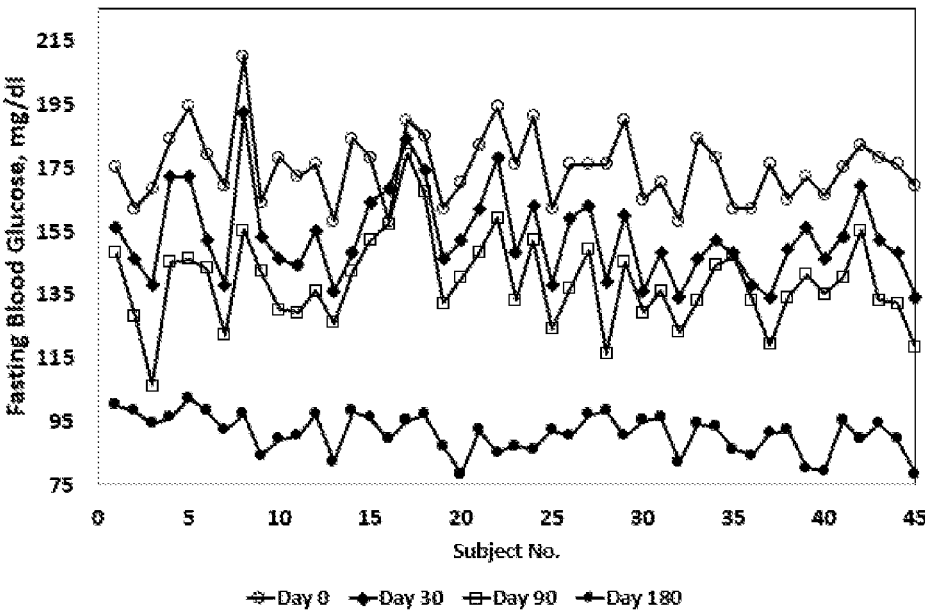
Figure 5:
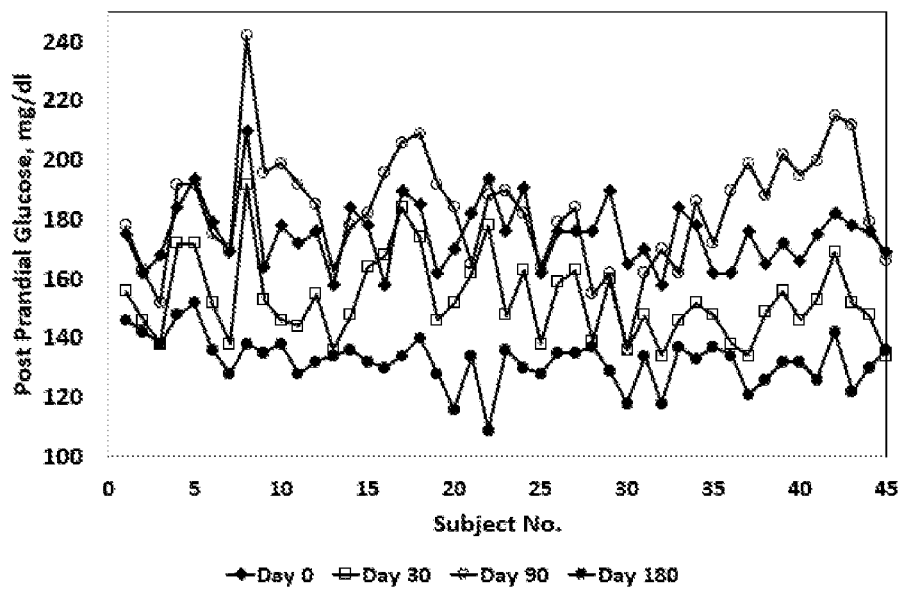
Figure 6:
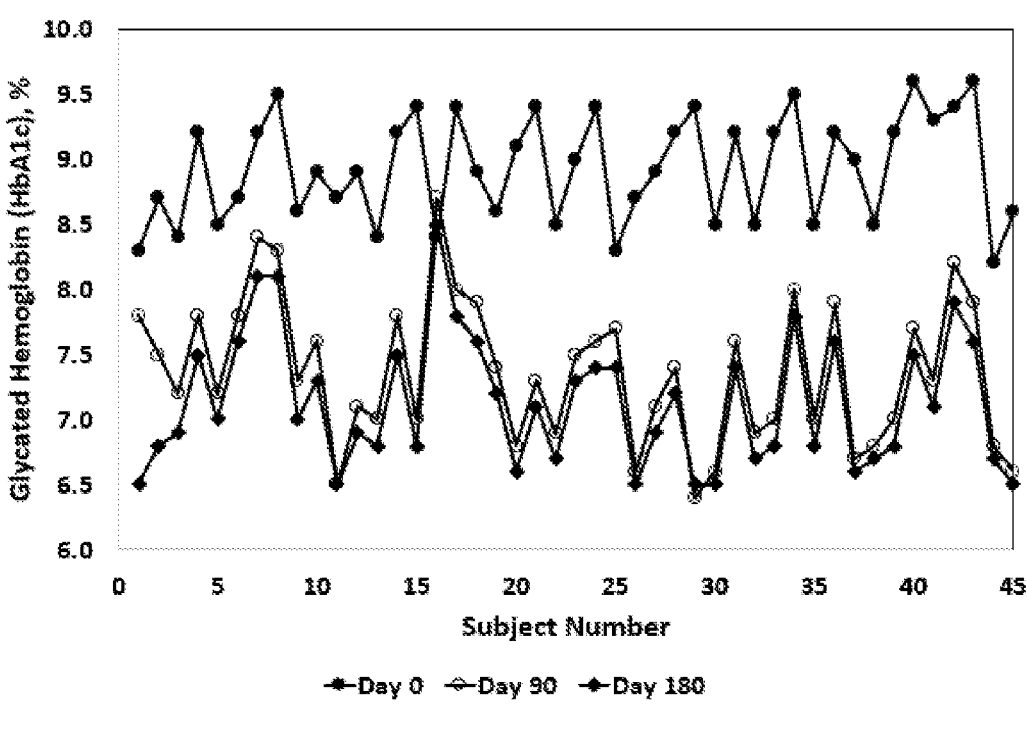
Figure 7:
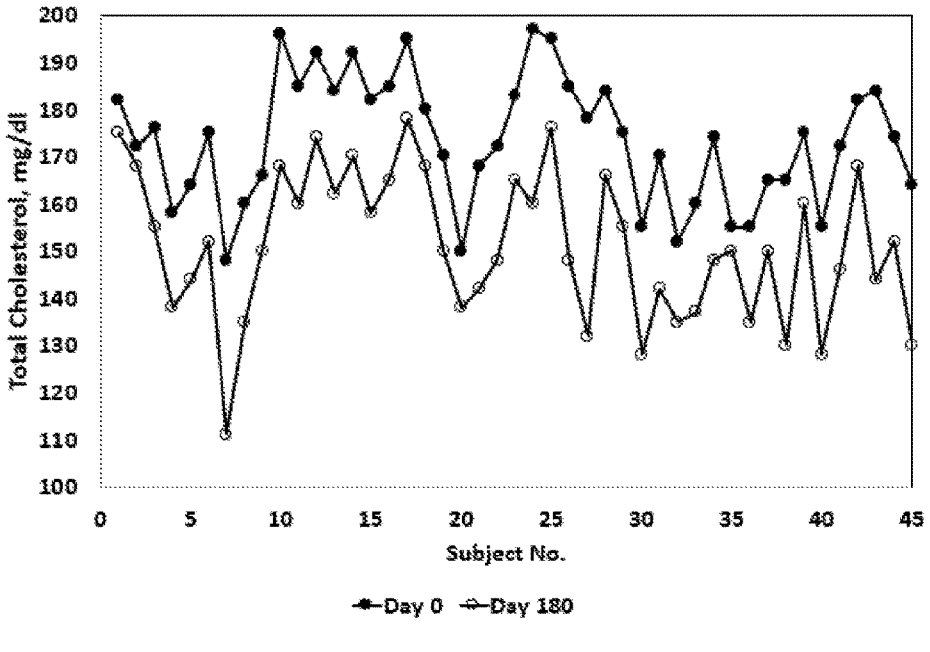
Figure 8:
Figure 8:
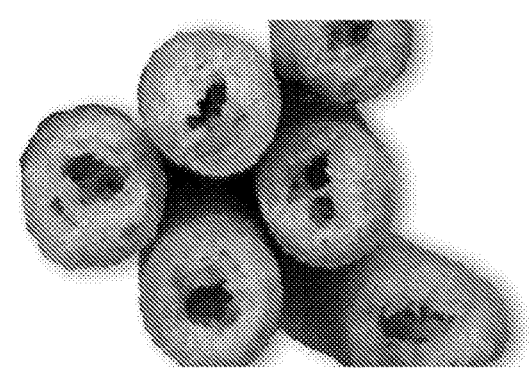

It is to be noted, however, that the appended drawings illustrate only typical embodiments of the present subject matter and are therefore, not to be considered for limiting of its scope, for the subject matter may admit to other equally effective embodiments: FIG. 1 defines Fasting Blood Glucose (FBG) Trends from 10-person, 90 day clinical trial FIG. 2 defines Post Prandial Blood Glucose Trends, 2 hours after breakfast from 10-person 90 day clinical trial FIG. 3 defines Post Prandial Blood Glucose Trends, 2 hours after lunch from 10-person 90 day clinical trial FIG. 4 defines Fasting Blood Glucose (FBG) Trends from 45-person, 180 day clinical trial FIG. 5 defines Post Prandial Blood Glucose (PPBG) Trends from 45-person, 180 day clinical trial measured two hours after breakfast FIG. 6 defines Glycated Hemoglobin (HbA1c) Trends from 45-person, 180 day clinical trial FIG. 7 defines Total Cholesterol Trends from 45-person, 180 day clinical trial FIG. 8 illustrates a Cross Sectional Views of Foxtail Millet/Murukku—Control versus herbal treatment

DETAILED DESCRIPTION

The following presents a detailed description of various embodiments of the present subject matter with reference to the accompanying drawings.

The embodiments of the present subject matter are described in detail with reference to the accompanying drawings. However, the present subject matter is not limited to these embodiments which are only provided to explain more clearly the present subject matter to a person skilled in the art of the present disclosure.

As used herein, the singular forms "a", "an" and "the" are intended to include the plural forms as well, unless expressly stated otherwise. It will be further understood that the terms "includes", "comprises", "including" and/or "comprising" when used in this specification, specify the presence of stated features, integers, steps, operations, elements, and/or components, but do not preclude the presence or addition of one or more other features, steps, operations, elements, components, and/or groups thereof. As used herein, the term "and/or" includes any and all combinations of one or more of the described ingredients having similar properties.

The subject matter described herein relates to a method of improving functional and organoleptic properties of natural products and nutraceutical composition(s) thereof for the better management of diabetes.
Multi Herbal System Requirement Most single herbs and spices to provide a particular functionality exhibit certain predominant mechanism of action.

If we take management of blood glucose in the human body, there are multiple processes that commence with enzymatic processes that breakdown complex carbohydrates into simple sugars such as glucose or fructose which have to be further synthesized in the human system through Krebs cycle for releasing the energy requirements in the body. These are complex processes known to those skilled in human physiology. A single herb or spice or plant may deliver one or more active ingredients that can impact a particular blood glucose management pathway.

Due to diversity of physiology among humans, there could be one or more pathways that are deficient in the human blood glucose management pathway. By consuming one herb they may or may not effectively address the needs of a particular individual in managing their blood glucose levels. A multi-herbal system can address these short comings by simultaneously addressing various blood glucose management pathways and therefore the probability of a multi-herbal system to address the blood glucose management deficiencies increases significantly.

Consuming Many Herbs

While consuming multiple herbs would greatly help with addressing blood glucose management needs of many individuals, the challenges of developing and consuming multiple herbs daily poses several difficulties: 1. Identification of effective herbal formulation of multiple herbs; 2. Most of the herbs could only be effective when consumed in huge quantities lifelong which is humanly not possible; 3. The organoleptics of most natural materials are not suitable for daily consumption to deliver benefits continuously, 4. Achieving patient compliance remains a challenge with herbal formulations. The above are the most primary roadblocks towards development and administration of a multi-herbal formulations from the all the other issues known to a person skilled in the art.

Quantity of Herbs

The quantity of each of the herbs to deliver the required functionality is often large. For example, separate clinical studies have shown the need to consume 100 g of Fenugreek, 30 g of Indian Gooseberry or Amla to deliver HbA1c or 3-month average blood glucose average benefits. Consuming such large quantity of herbs makes it very difficult to comply. This is due to low solubility of active ingredients in water. Most beneficial properties are delivered to a particular organ in a water-soluble form to deliver benefits.

The multi-herbal system of the present invention, with the active ingredients in a water-soluble form, the current invention delivers all the benefits of multiple herbs in a water-soluble form that have shown to delivery benefits to a much larger cross section of subjects who may individually require assistance from specific target mechanisms which can differ from individual to individual. While the examples contained herein describe the specifics for blood glucose management and low oil absorbing functionality from the set of herbs selected, the process can deliver the necessary functionalities for other diseases or disorders by careful selection of the required mix of herbs, spices, plants or natural materials. Further as products from this invention are water based, they can be used to fortify many foods and beverages to deliver the efficacy and benefits.

Deep Fried Foods

Deep frying is a common cooking method used across the globe. It's often used by restaurants and fast-food chains as a quick and inexpensive way to prepare foods.

Generally speaking, fried foods are significantly higher in fat and calories than their non-fried counterparts. For example, one small baked potato (100 grams) contains 93 calories and 0 grams of fat, while the same amount (100 grams) of french fries contain 319 calories and 17 grams of fat.

A recent prospective cohort study quantified risk parameter on association of fried food consumption in US with all cause, cardiovascular, and cancer mortality. The study summarized results as follows:

31 558 deaths occurred during 1 914 691 person years of follow-up. For total fried food consumption, when comparing at least one serving per day with no consumption, the multivariable adjusted hazard ratio was 1.08 (95% confidence interval 1.01 to 1.16) for all-cause mortality and 1.08 (0.96 to 1.22) for cardiovascular mortality. When comparing at least one serving per week of fried chicken with no consumption, the hazard ratio was 1.13 (1.07 to 1.19) for all-cause mortality and 1.12 (1.02 to 1.23) for cardiovascular mortality. For fried fish/shellfish, the corresponding hazard ratios were 1.07 (1.03 to 1.12) for all-cause mortality and 1.13 (1.04 to 1.22) for cardiovascular mortality. Total or individual fried food consumption was not generally associated with cancer mortality.

The study further concluded that frequent consumption of fried foods was associated with a higher risk of all cause and cardiovascular mortality in women in the US.

Deep fried foods consumption is on the rise globally. Popular fried foods include potato chips, French fries, fish and chicken strips, cheese sticks and savories like Murukku (chakli), Boondi are popular among most people. The energy density of these foods is very high and it is one of the important causative factors for rising obesity levels which in turn lead to many diseases and disorders such as diabetes, hypertension and cardio vascular disease. It is therefore another object of this invention is to lower oil uptake during deep fat frying.

Herbs & Spices used in current invention

The object of the present invention is to provide a herbal composition comprising herbs from different families such as Cinnamon (*Cinnamomum verum*), Ginger (*Zingiber officinale*), Coriander Seeds (*Coriandrum sativum* L.), Star Anice (*Illicium verum*), Turmeric (*Curcuma longa*), Cumin (*Cuminum cyminum*), Black Cumin (*Nigella sativa*), Fenugreek (*Trigonella foenum-graecum*), Black Pepper (*Piper nigrum*), Clove (*Syzygium aromaticum*), Indian Gooseberry or Amla (*Phyllanthus emblica*), Black Plum or Black Jamun (*Syzygium cumini*), Indian *Senna* (*Senna alexandrina*), Guava Leaves (*Psidium guajava*), White Pepper (*Piper Nigrum*), Ajwain (*Trachyspermum ammi*), and Fennel Seeds (*Foeniculum vulgare*) family for prevention and treatment of diabetes and a method for the preparation thereof.

The herbal composition disclosed in the present invention is useful for managing the risk of diabetes, lipids and obesity. Fortification of foods with these herbs and spices either directly or after further processing can deliver herbal water in its native form or through fortification of various products with lower the absorption of oils during deep fat frying.

The composition comprises a therapeutically effective number of herbs. Furthermore, a brief description of medicinal herbs families is given below.

*Cinnamomum verum*, commonly known as Cinnamon is the inner bark of a tropical evergreen tree. Since it is delicate in flavor, cinnamon is used in dessert dishes, cakes and other baked recipes. The spice is used in Indian curries and forms a part of the garam masala. Cinnamon intake appears to increase insulin efficiency such that less insulin is required. It has also been found to lower serum glucose, triglyceride, LDL cholesterol, and total cholesterol in people with type 2 diabetes and this can reduce risk factors associated with diabetes and cardiovascular diseases. Consumption of 1 g per day of cinnamon in randomized clinical studies resulted in 0.83% reduction in HbA1c in 90 days.

Ginger is an underground rhizome of plant *Zingiber officinale* belonging to the family Zingiberaceae, and it is one of the most widely consumed spices worldwide. Anti-diabetic, hypolipidemic and anti-oxidative properties of ginger have noticed in several types of research. Ginger contains several potentially bioactive substances, mainly gingerols and their related dehydration products, the shogaols, as well as volatile oils including sesquiterpenes, such as beta-bisabolene and (-)-zingiberene, and monoterpenes, mainly geranial and neral. Ginger pretreatment inhibited the induced hyperglycemia and hypoinsulinemia. Oral administration of ginger powder for 12 weeks at a dose of 2 g per day caused a significant reduction in the levels of FBS, HbA1c.

Coriander seeds or *Coriandrum sativum* L. are said to be useful in managing diabetes. These seeds, which are used to add extra flavour to dal, curries and other delicacies, comprise essential nutrients like potassium, iron, vitamin A, C and K, folic acid, magnesium, and calcium. Due to the presence of such nutrients, coriander seeds are said to reduce blood glucose levels in diabetics and maintain the insulin activity, which further helps in keeping blood sugar levels in check. Clinical studies have found that the extracts from coriander seeds have certain compounds that when discharged into the blood caused anti-hyperglycaemic, insulin discharging and insulin like movement that can help keep your blood glucose levels in control.

Star Anice or *Illicium verum* is rich in antioxidants and vitamin A and C, which help fight free radicals that are responsible for early ageing and diabetes. Some research indicates that anethole, the active ingredient in anise seed, may keep blood sugar levels in check when paired with a healthy diet.

Turmeric or *Curcuma longa* is gaining a growing interest in the scientific community of medicinal plants. The active ingredient in turmeric, curcumin, is a bioactive molecule present in the rhizome of the *Curcuma longa* plant, also known as turmeric. Curcumin has a potential role both in the prevention and treatment of several diseases because of its variety of actions: anti-bacterial, anti-diabetic, anti-viral and anti-cancer activities. Curcumin improves the pathologic events in T2DM through different mechanisms and multiple molecular targets. Curcumin can improve insulin sensitivity by decreasing glycaemia and dyslipidaemia. Oxidative stress has related to the pathogenesis of T2DM. The protective effect of Curcumin against oxidative damage has proven. Curcumin reduces the lipid peroxidation by normalization of antioxidant enzyme levels like superoxide dismutase, catalase and glutathione peroxidase. Curcumin was also shown to reduce postprandial glycaemic response and insulin demand for blood glucose control.

*Cuminum cyminum* commonly known as cumin seeds has been consumed in Indian cuisine for thousands of years. Cumin seeds or dried cumin powder is commonly added to food to enhance its taste and flavor. It is also used for flavoring rice. Cumin, which is called 'Jeera' in Hindi language is used as part of jeera rice in north Indian cuisine. Some studies have shown that antidiabetic potential of cumin seeds is attributed to the presence of thymoquinone, an active chemical component that protects the β-cells of the pancreas from oxidative stress. It also helps in increasing the production of insulin in the body, thereby aiding in keeping the blood glucose under control. Clinical studies have revealed that a dose of 2 gm/day showed significant reductions in fasting blood glucose, post prandial blood glucose (2 hours post meals) and HbA1c.

Black Cumin or *Nigella sativa* was shown to be effective in treating diabetes by enhancing insulin production, glucose tolerance, and beta cell proliferation. Studies have concluded that the seeds also can play a significant role in the treatment of diabetes complications such as nephropathy, neuropathy, and atherosclerosis. In long term studies 3 gm/day consumption of Black Cumin was shown to cause reductions in Fasting Glucose levels, HbA1c or three month average blood glucose levels. *Nigella Sativa* lowered insulin resistance and improved β-cells performance of the pancreas.

Fenugreek or *Trigonella foenum-graecum*, commonly known as Fenugreek seeds is cultivated worldwide as a semiarid crop. Its seeds and its leaves are common ingredients in dishes from South Asia. Fenugreek seeds are high in soluble fiber, which helps lower blood sugar by slowing down digestion and absorption of carbohydrates. Fenugreek seeds are a rich source of vitamins, minerals and antioxidants and thereby provide excellent nutritional benefits.

Black Pepper or *Piper nigrum* is a spice that belongs to the family Piperaceae. It has more than 1000 species and is a widely used spice. The distinct biting quality attributed to piperine and its isomers. Based on animal studies it was found that oral administration of *Piper longum* dried fruit has shown significant anti-hyperglycaemic, antioxidant and anti-lipid peroxidative effects. Black pepper oil has radical scavenging and ferric reducing antioxidant abilities. Oxidative stress is the major contributor to diabetes, and piperine has antioxidant potential. The combination of turmeric, black pepper and adjacent seed powder possesses anti-hyperglycemic, anti-hyperlipidaemic activity in diabetes mellitus.

Clove or *Syzygium aromaticum* is a herbal plant which belongs to the species *aromaticum* genus *Syzygium* and family *Myrtaceae*. Clove contains eugenol, isoeugenol and caryophyllene compounds. The main components in the *Syzygium aromaticum* are Olaenic acid and Eugenol, and the glucose-lowering result of *Syzygium aromaticum* could be through the antioxidant property. *Syzygium aromaticum* has insulin-mimetic action and improves insulin efficiency by stimulation of functioning pancreatic beta cells, to increase the release of insulin. The anti-hyperglycemic effect of clove may be due to its inhibitory action on alpha-glucosidase.

Indian Gooseberry or Amla or *Phyllanthus emblica* is used in the Indian system of medicine and believed to increase defense in diseases. Vitamin C, tannins and flavonoids in amla have potent antioxidant properties. Amla is effective in reducing the Fasting and Post Prandial blood glucose levels and HbA1c levels. High vitamin C content of amla controls diabetes. A spoon of its juice mixed with bitter gourd juice, taken daily for 2 months will enhance the pancreas and enable it to secrete insulin, thus reducing the blood sugar in diabetes. Diet restrictions should strictly observe while taking this medicine. V. S. Muthusamya, S. Ananda, K. N. Sangeethaa, S. Sujathaa, Balakrishnan Arunb, B. S. Lakshmi; Chemico-Biological Interactions 174 (2008) 69-78 discusses the capacity of tannins to increase glucose uptake and inhibit adipogenesis makes them potential drugs for the treatment of non-insulin-dependent diabetes mellitus. The therapeutic approaches for decreasing postprandial hyperglycemia are to prevent or delay the absorption of glucose by the inhibition of carbohydrate hydrolyzing enzymes, aamylase and α-glucosidase, in the digestive organs.

Black Plum or Black Jamun or *Syzygium cumini* is an important indigenous plant of the family *Myrtaceae* originally from Indonesia and India. The fruit pulp is sweet, and seeds are acrid, sour, tonic. The pulp and seeds used for raditional medicine against diabetes. The seed, fruit, and bark of Jamun possess antidiabetic effects. As discussed in Sidana S, Singh V B, Meena B L, Beniwal S, Singh K, Kumar D, et al. Effect of *Syzygium cumini* (jamun) seed powder on glycemic control: A double-blind randomized controlled trial. J Med Soc 2017; 31:185-9, administering the standardized seed powder caused a significant decrease in the fasting blood sugar, insulin resistance, and increase in High-density lipoprotein (HDL;) cholesterol at the end of the third month. The Jamun possesses free radical scavenging and antioxidant effects, prevents lipid peroxidation, regenerates the 6-cells, prevents alterations in glyca ion status and formation of AGEs, improves glucose utilization and maintains glucose homeostasis, activates peroxisomal PPARs, inhibits alpha-glucosidases, and ameliorates dyslipidemia. The antidiabetic actions of Jamun may be due to stimulation of pancreatic insulin secretion, restoration of beta-cell architecture, reduction of oxidative stress and antioxidant effect, and amelioration of dyslipidemia. These activities are beneficial in reducing hyperglycemia and in preventing the secondary complications of diabetes.

Indian *Senna* or *Senna alexandrina* is historically, *Senna alexandrina* was used in the form of *senna* pods, or as herbal tea made from the leaves, as a laxative and also serves as a fungicide. Recent studies have also shown the plant species had significant α-amylase and α-glucosidase inhibitory activity. α-amylase inhibition slows down the breakdown of carbohydrates to glucose and inhibition of α-glucosidase therapy is beneficial to delay absorption of glucose after a meal.

Guava or *Psidium guajava* contains compounds that inhibit absorption of certain types of sugar and therefore lowers post prandial blood sugars. Guava leaf seems to lower fasting sugars as well. Several studies have shown guava leaf tea also reduces cholesterol and insulin levels. Broadly, a majority of the plant species had significant alpha amylase and alpha glucosidase inhibitory activity. From the in vitro results, it can be concluded that all the tested plants may have some merit in the management of diabetes mellitus type 2 diabetes which is discussed in 'Evaluation of six plant species used traditionally in the treatment and control of diabetes mellitus in South Africa using in vitro methods' N. K. K. Boaduo, D. Katerere, J. N. Eloff & V. Naidoo.

White Pepper or *Piper Nigrum* and black pepper come from the same peppercorn plant, but how they are processed produces the difference in flavour. White pepper naturally inhibits two enzymes that break down starch into glucose. This effect may help regulate blood glucose and delay glucose absorption and these two effects are called α-amylase and α-glucosidase enzyme inhibition processes.

Ajwain or *Trachyspermum ammi* also called Carom seeds are incredibly nutritious, being rich in fiber, antioxidants, and other vitamins and minerals. Because of this, they have been associated with health benefits and long been used in traditional Indian medicine practices. Ajwain seeds help regulate blood glucose and delay glucose absorption and these two effects are called aamylase and α-glucosidase enzyme inhibition processes Fennel Seeds or *Foeniculum vulgare* high source of nutrients like vitamin C and Potassium, it helps in lowering the blood sugar levels and also helps to increase insulin reactivity resulting in balancing the sugar.

The current invention relates to a herbal formulation of the above herbs and spices to provide active ingredients from these herbs and spices to provide adjunctive support to diabetics, pre-diabetics and wellness conscious consumers and to also lower oil uptake of foods fortified with herbal extract during deep fat frying.

Storage of Herbs and Spices

Herbs and spices can effectively be stored for periods of up to 1-2 years without losing potency and efficacy. Each of the herbs and spices used in the formulation have optimal storage and moisture content to minimize growth of yeast, mold and various organisms. The moisture content of all the dried herbs or spices used in the herbal formulation of the present invention should be between 5% to 25% based on the nature of the component. Further, for any fresh ingredient like fresh ginger and the like the moisture content should not be more than 80% to 85%.

Grinding Herbs and Spices

The herbs and spices used in the current invention are ground under controlled conditions. The grinding conditions are optimized to achieve the desired particle size by using a hammer mill. The grinding time, grinding mill rpm and maximum herbal powder temperature to minimize thermal degradation of herbs and spices are summarized in Table 1.

TABLE 1

| | | | | | | Target average particle size | Preferred Grinding particle size | Preferred Grinding Time | Herbal Powder Temperature | Preferred Temperature of herbs during grinding |
|---|---|---|---|---|---|---|---|---|---|---|
| Ingredient | Scientific Name | Primary Mill | Hammer Mill RPM | Typical Batch Size | Grinding Time | | | | | |
| Cinnamon | *Cinnamomum verum* | Hammer Mill | 1600 | 100 kg | 5 min-1 hr | 30-300 microns | 80-90% through 100 Mesh (149 microns) | 30 min | 10-75 deg C. | 50 deg C. |
| Ginger | *Zingiber officinale* | Hammer Mill | 1600 | 100 kg | 5 min-1 hr | 30-300 microns | 80-90% through 100 Mesh (149 microns) | 30 min | 10-75 deg C. | 50 deg C. |
| Coriander Seeds | *Coriandrum sativum L.* | Hammer Mill | 1800 | 100 kg | 5 min-1 hr | 30-300 microns | 80-90% through 100 Mesh (149 microns) | 30 min | 10-75 deg C. | 50 deg C. |
| Star Anice | *Illicium verum* | Hammer Mill | 1600 | 100 kg | 5 min-1 hr | 30-300 microns | 80-90% through 100 Mesh (149 microns) | 30 min | 10-75 deg C. | 50 deg C. |
| Turmeric | *Curcuma longa* | Hammer Mill | 1600 | 100 kg | 5 min-1 hr | 30-300 microns | 80-90% through 100 Mesh (149 microns) | 30 min | 10-75 deg C. | 50 deg C. |
| Cumin | *Cuminum cyminum* | Hammer Mill | 1800 | 100 kg | 5 min-1 hr | 30-300 microns | 80-90% through 100 Mesh (149 microns) | 30 min | 10-75 deg C. | 50 deg C. |
| Black Cumin | *Nigella sativa* | Hammer Mill | 1800 | 100 kg | 5 min-1 hr | 30-300 microns | 80-90% through 100 Mesh (149 microns) | 30 min | 10-75 deg C. | 50 deg C. |

TABLE 1-continued

Grinding Conditions for Herbs & Spices

| Ingredient | Scientific Name | Primary Mill | Hammer Mill RPM | Typical Batch Size | Grinding Time | Target average particle size | Preferred Grinding particle size | Preferred Grinding Time | Herbal Powder Temperature | Preferred Temperature of herbs during grinding |
|---|---|---|---|---|---|---|---|---|---|---|
| Fenugreek | *Trigonella foenumgraecum* | Hammer Mill | 1800 | 100 kg | 5 min-1 hr | 30-300 microns | 80-90% through 100 Mesh (149 microns) | 30 min | 10-75 deg C. | 50 deg C. |
| Black Pepper | *Piper nigrum* | Hammer Mill | 1800 | 100 kg | 5 min-1 hr | 30-300 microns | 80-90% through 100 Mesh (149 microns) | 30 min | 10-75 deg C. | 50 deg C. |
| Clove | *Syzygium aromaticum* | Hammer Mill | 1800 | 100 kg | 5 min-1 hr | 30-300 microns | 80-90% through 100 Mesh (149 microns) | 30 min | 10-75 deg C. | 50 deg C. |
| Indian Gooseberry (Amla) | *Phyllanthus emblica* | Hammer Mill | 1600 | 100 kg | 5 min-1 hr | 30-300 microns | 80-90% through 100 Mesh (149 microns) | 30 min | 10-75 deg C. | 50 deg C. |
| Black Plum (Black Jamun) | *Syzygium cumini* | Hammer Mill | 1600 | 100 kg | 5 min-1 hr | 30-300 microns | 80-90% through 100 Mesh (149 microns) | 30 min | 10-75 deg C. | 40 deg C. |
| Indian Senna | *Senna alexandrina* | Hammer Mill | 1600 | 100 kg | 5 min-1 hr | 30-300 microns | 80-90% through 100 Mesh (149 microns) | 30 min | 10-75 deg C. | 50 deg C. |
| Guava Leaves | *Psidium guajava* | Hammer Mill | 1800 | 100 kg | 5 min-1 hr | 30-300 microns | 80-90% through 100 Mesh (149 microns) | 30 min | 10-75 deg C. | 50 deg C. |
| White Pepper | *Piper Nigrum* | Hammer Mill | 1800 | 100 kg | 5 min-1 hr | 30-300 microns | 80-90% through 100 Mesh (149 microns) | 30 min | 10-75 deg C. | 40 deg C. |
| Ajwain | *Trachyspermum ammi* | Hammer Mill | 1800 | 100 kg | 5 min-1 hr | 30-300 microns | 80-90% through 100 Mesh (149 microns) | 30 min | 10-75 deg C. | 50 deg C. |
| Fennel Seeds | *Foeniculum vulgare* | Hammer Mill | 1800 | 100 kg | 5 min-1 hr | 30-300 microns | 80-90% through 100 Mesh (149 microns) | 30 min | 10-75 deg C. | 50 deg C. |

Organoleptic Properties enhancement of Herbs and Spices

The word, "organoleptic" used in English comes from the French word organoleptique, which derives from "organ" (same meaning as in English) and Greek leptikos, meaning "disposed to take or accept."

The term organoleptic properties are the aspects of food, water or other substances that an individual experiences via the senses. Sensory Evaluation is a scientific discipline used to evoke, measure, analyze, and interpret those responses to products that are perceived by the senses of sight, smell, touch, taste, and hearing. The terms Organoleptic and Sensory Evaluation are now used interchangeably.

Organoleptic properties are the aspects of food, water or other substances that create an individual experience via the senses—including taste, sight, smell, and touch. In addition to these, properties such as mouth feel, appearance, bouquet, aroma, and after taste become a very important aspect of a consumer experience and fall within the scope of organoleptic properties or sensory evaluations.

The current invention relates to the process of a process of enhancing organoleptic properties of natural products and nutraceuticals thereof. More specifically they involve use of many herbs and spices. These herbs and spices, while possessing many health and wellness properties, provide many properties in food preparations such as color, flavor, aroma and texture. In order to provide the necessary benefits, they have to be consumed in large quantities in their native form.

For example, a clinical study titled, "Effectiveness of Fenugreek for Lowering

Hemoglobin (HbA1c) in Patients with Self-Management of Type 2 Diabetes: A Randomized Controlled Trial" by Ansari R, Ansari S, published in Intech Open, www.intechopen.com, September 2011, 100 g of Fenugreek was consumed by participants in clinical trial to lower long term blood sugar values as measured by Glyacated Hemoglobin or HbA1c.

Similar studies were conducted with other herbs, spices or foods where 10 g of Black Jamun (ref: Sidana S, Singh V B, Meena B L, Beniwal S, Singh K, Kumar D, et al. Effect of *Syzygium cumini* (jamun) seed powder on glycemic control: A double-blind randomized controlled trial. J Med Soc 2017; 31:185-9.) was consumed by subjects or 30 g per day of Amla was consumed (Santhi Sri K V, Jalaja Kumari D, Sivanarayana G, Effect of Amla, an approach towards the control of Diabetes mellitus, Int.J.Curr.Microbiol.App.Sci (2013) 2(9): 103-108). Consuming such large quantities of these foods in their native forms daily for extended periods of time become difficult and impractical.

The current invention of extracting the necessary ingredients into a water format and a relatively pleasing taste allows the required efficacy or functionality to be delivered in an easily consumable format.

One objective of this invention is to provide beneficial properties of these herbs and spices to enable easy and daily consumption of these herbs and spices in an easy to consume water format to assist in blood glucose management among diabetics and pre-diabetics.

Second application of significant utility is to fortify various flours and spices with the herbal extract ingredients which cause a significantly lower oil absorption characteristics in deep fried foods. The fortified flours and legumes from this invention enable significant reduction in fat and calories contained in deep fried foods which are greatly contributing towards obesity all over the world. In one of the embodiments of the present invention it discloses method for manufacturing a formulation of natural products comprising herbs, plants and/or spices and/or part thereof with enhanced functional and organoleptic properties comprising the steps of:

o. Selection of herbs and/or spices p. Grinding of herbs and/or spices under controlled condition(s) to a desired particle size q. Mixing of the herbs of step p.

r. The resultant powder of step q is homogenized with water and made into a slurry form The herbs and/or spices used in the method are selected with the moisture content, when dried 5% to 25%, and when fresh with 80% to 85%. Further, the grinding performed in the method is preferably done by hammer mill or commercial food shredder pulveriser. The hammer mill is operated preferably between 1500 RPM-2000 RPM and more preferably between 1600 RPM-1800 RPM. The desired particle size of the constituents achieved by the grinding process preferably ranges between 30 microns-300 microns for manufacturing a formulation with desired properties of the present invention. The method as discussed above, the step c for manufacturing a slurry formulation and/or formulation in a filtrate further comprises the following steps:

h. The herbal formulation of step (c), is dissolved in desired quantity of water.

i. The mixture of step (a) is kept in a jacketed stirred tank for about 4-16 hours at a temperature of 25 deg C. to 60 deg C.

j. The slurry of step (b) is filtered under pressure k. Distillation of the filtrate of step c l. Distillation of the slurry of step c m. Organoleptic herbal concentrate was collected n. The filtrate of step (d) optionally be filtered In yet another embodiment the method of the present invention, in the step c for the manufacturing a slurry formulation and/or formulation in a filtrate alternatively may further comprises the following steps:

s. The herbal formulation obtained by the above method in step (c), is dissolved in desired quantity of water.

t. The mixture of step (a) is kept in a jacketed stirred tank for about 4-16 hours at a temperature of 25 deg C. to 60 deg C.

u. The slurry of step (b) is filtered under pressure v. Contacting the filtrate with activated carbon with a BET surface area of 500-1,700 sq metres per gram for a period of 30-60 minutes at a temperature of 35-65 deg C.

w. Herbal filtrate after treatment with activated carbon is collected after removal of color and taste causing compounds In yet another embodiment the method of the present invention, in the step c for the manufacturing a slurry formulation and/or formulation in a filtrate alternatively may further comprises the following steps:

x. The herbal formulation obtained by the above method of step (c), is dissolved in desired quantity of water.

y. The mixture of step (a) is kept in a jacketed stirred tank for about 4-16 hours at a temperature of 25 deg C. to 60 deg C.

z. The slurry of step (b) is filtered under pressure aa. Contacting the filtrate in an ion-exchange column containing anionic polymers such as microporous grade polystyrenic strong base type I anion exchanger having quarternary ammonium functional groups, non-ionic polydivinyl benzene adsorbant resins, styrene matrix and acrylic matrix resins with BET surface area of 500-1,200 sq metres per gram bb. Herbal filtrate after treatment with ion exchange column is collected after removal of color and taste causing compounds The method as disclosed in the present invention, the distillation of step (c) was performed in vacuum between 0.01 torr to 300 torr, preferable range between 0.05 to 100 torr. The temperature of step (b) could preferably between 25 to 55 deg C. Further, the filtration of step (c) is preferably carried out by plate and frame or membrane press operating at pressures ranging between 2 to 15 bars. The distillation of step (d) is preferably carried out in a rotary evaporator. Said evaporator is immersed in the heated water bath or water/glycol bath and is preferably rotated at 40-70 rpm. The evaporator is further fitted with the condenser cooled with chilled water or water/glycol mixture. The condenser is further connected with a vacuum pump operating at vacuum levels between 0.05 torr to 100 torr. The residence time for the batch preferably ranges from 3 hours to 12 hours. The distillation of slurry is preferably done by glass batch distillation and which is preferably provided with a impeller. The glass batch distillation is preferably immersed in a heater oil batch. Further, the batch distillation is condensed preferably in a shell and tube condenser. Said condenser is preferably chilled with water or w water/glycol water/glycol ater/glycol mixture to condense the vapor. The distillation/condenser unit(s) is operated at vacuum levels between 0.01 torr to 100 torr. The residence time for the batch preferably ranges from 3 hours to 12 hours.

The distillation step (d) can also be carried out in other types of distillation equipment such as wet film evaporator (WFE) or agitated thin film evaporator (ATFE) or agitated thin film distillation (ATFD) device.

Further, the method as disclose in the present invention above, the slurry of step b may optionally be charged to an Agitated Thin Film Evaporator (ATFE) or Wet Film Evaporator (WFE). The system is preferably operated under vacuum ranging from 0.01 torr to 100 torr and the residence time in the ATFE unit preferably varies from 1 second to 60 seconds. The range of overall herbal extract recoveries from batch distillation to ATFE ranges from 40% to 95%.

The distillation step (d) can also be carried out in other types of distillation equipment such as rotary evaporator and wet film evaporator (WFE).

Yet another object of the present subject matter is to provide for nutraceutical formulations for diabetes management and low-fat absorbing foods for weight management benefits. A primary objective of the current invention is to produce nutraceutical supplements in a highly efficacious and effective form.

A herbal Formulation for the treatment and management of diabetes comprising essentially of a therapeutically effective amount of *Coriandrum sativum* L., *Illicium verum, Curcuma longa, Cuminum cyminum, Nigella sativa, Trigonella foenum-graecum, Piper nigrum, Syzygium aromaticum, Zingiber officinale, Phyllanthus emblica, Syzygium cumini, Cinnamomum verum, Senna alexandrina, Psidium guajava, Piper Nigrum, Trachyspermum ammi, Foeniculum vulgare*. The aforesaid herbal formulation broadly comprises of the herbal constituents in the range of *Coriandrum sativum* L. 0.0-10.0%, *Illicium verum* 0.0%-5.0%, *Curcuma longa* 1.0%-15.0%, *Cuminum cyminum* 0%-20.0%, *Nigella sativa* 0.0%-20.0%, *Trigonella foenum-graecum* 2.0%-20.0%, *Piper nigrum* 5.0%-20.0%, *Syzygium aromaticum* 1.0%-20.0%, *Zingiber officinale* 1.0%-20.0%, *Phyllanthus emblica* 3.0%-35.0%, *Syzygium cumini* 5%-60.0%, *Cinna-*

*momum verum* 1.0%-20.0%, *Senna alexandrina* 0.0%-50.0%, *Psidium guajava* 0.0%. 7.5%, *Piper Nigrum* 0.0%-5.0%, *Trachyspermum ammi* 0.0%-7.5% and *Foeniculum vulgare* 0.0%-5.0%.

The herbal formulation of the present invention could be manufactured using parts of the plants used for preparing the extracts are *Coriandrum sativum* L. Seeds, *Illicium verum* Fruit, *Curcuma longa* Root., *Cuminum cyminum* Seeds, *Nigella sativa* Seeds., *Trigonella foenum-graecum* Seeds., *Piper nigrum* Fruit, *Syzygium aromaticum* Flower Buds, *Zingiber officinale* Root., *Phyllanthus emblica* Fruit., *Syzygium cumini* Fruit & Seed, *Cinnamomum verum* Bark, *Senna alexandrina* Leaves, Flower and Stem, *Psidium guajava* Leaves & Fruit, *Piper Nigrum* Fruit, *Trachyspermum ammi* Fruit, *Foeniculum vulgare* Fruit. The formulation could be in the form of powder, slurry or filtrate, etc. Also, food product(s) treated and/or fortified with the herbal formulation to achieve desired results. The food products so formed have improved HbA1c, FBG, PPBG and lipids levels. Thus said food products could be used for disease management and better health like diabetes mellitus by the administration of an effective amounts of the formulation. An added advantage of the formulation is that the oil absorption of deep-fried foods treated with the formulation reduces by 10% to 45%.

As yet another embodiment the herbal formulation constituents are present in the range of *Syzygium cumini* 35%, *Phyllanthus emblica* 12.0%, *Piper nigrum* 10.0%, *Trigonella foenum-graecum* 10.0%, *Curcuma longa* 10.0%, *Cinnamomum verum* 7.5%, *Syzygium aromaticum* 7.5% and *Zingiber officinale* 7.5%.

As another embodiment the herbal formulation of the present invention comprises of the herbal constituents present in the range of *Coriandrum sativum* L. 1.0%, *Illicium verum* 1.0%, *Curcuma longa* 4.0%, *Cuminum cyminum* 5.0%, *Nigella sativa* 5.0%, *Trigonella foenum-graecum* 5.0%, *Piper nigrum* 6.0%, *Syzygium aromaticum* 3.5%, *Zingiber officinale* 6.0%, *Phyllanthus emblica* 7.0%, *Syzygium cumini* 15.0%, *Cinnamomum verum* 5.0%, *Senna alexandrina* 28.0%, *Psidium guajava* 2.5%, *Piper Nigrum* 1.5%, *Trachyspermum ammi* 2.0% and *Foeniculum vulgare* 2.5%.

In yet another embodiment the present invention discloses use of herbal water condensate as direct consumption or admixed with water, in fortified beverages, dairy applications and meal replacement shakes for management of blood glucose, improvement in HbA1c, FBG, PPBG, lipids levels, etc. for the better treatment and management of diabetes more particularly diabetes mellitus, heart related ailments. Further, fortification of grains and legumes with water based herbal water condensate disclosed in current invention reduces oil consumed during deep fat frying which lowers the calorific intake and helps in weight management, reduction in heart ailments from high lipids levels and the like.

Process for Enhancing functional and Organoleptic Properties & Products thereof of natural origin Step 1: Selection of Natural Products:

Many natural products such as oils of plant and animal origin, herbs, spices, plant materials, flowers, seeds, and leaves possess neutraceutical values that can address various disorders and diseases. However, the required ingredients that impart these properties normally tend to be found in these nutraceuticals in limited proportions. In addition to this, each of these natural materials comes with its own color, taste, smell and various unique organoleptic properties. In most cases these herbs and spices may be good for imparting specific taste, smell, texture or color to foods but are not normally suited for consuming large quantities.

Step 2: Storage of Ingredients:

All of the ingredients from the plant kingdom contain these beneficial ingredients which have to be harvested and sourced during the growing season. These herbs and spices have a natural tendency to absorb moisture. If there is excessive moisture content this will facilitate growth of yeast, mold and other organisms. The moisture content of 5-25% is an optimal range which has shown to be acceptable from the perspective of not negatively impacting shelf life. Some of these natural products need to be stored in a covered storage container whereas others can be stored in an open container. Storing these ingredients in controlled conditions allow for active ingredients to be intact without microbial contamination or loss of effectiveness throughout the year and thereby allow uninterrupted supply of ingredients with required efficacy.

Step 3: Grinding of Herbs and Spices:

The ingredients used in the formulation are taken in the said proportion. Each ingredient is then ground to a particle size that ranges between 30 to 300 microns. If the products are too finely ground there is a significantly higher energy that is used to lower the particle size. This energy input to these ingredients can cause higher heat levels which has a tendency to damage phytochemicals and desired active ingredients. Thermal degradation of these active ingredients can be reduced during grinding process by surrounding the grinding chamber with a cooling liquid or by blowing chilled air or nitrogen to lower the surface temperature during grinding process. Further, a very fine grind causes increase in viscosity when these ingredients are slurried as part of the process. Grinding the ingredients coarsely has the potential of increasing the time required to soak the ingredients in water to increase solubility of the desired active ingredients. An optimal particle size from 30-300 microns provides an optimal product size reduction to balance grinding thermal degradation, viscosity of slurry and slurry preparation time. Each of the herbs are ground to the desired particle size separately in order to provide optimal grinding with minimal thermal degradation.

Step 4: Slurry Preparation:

The ingredients required for the formulation are mixed in a conical blender or ribbon mixer to homogenize the mix. The resultant powder is slurried with water and kept in an agitated condition. The slurry is prepared in a jacketed stirred tank to keep the slurry in uniform suspension. The temperature of the slurry is maintained between 25 deg C. to 60 deg C. preferably between 25 to 45 deg C. for a period ranging from 4 to 16 hours. Step 5: Filtration of Slurry The resultant slurry is filtered using a plate and frame or membrane press operating at pressures ranging between 2 to 15 bars. The filtration is enhanced with diatomaceous earth filtration to enhance the rate of filtration. Preferred filter press used for filtering the herbal solids is membrane press operating at a fill cycle pressure of 5 to 7 bar and squeeze cycle pressure of 15 bar. The filtration yield of 58% is typically achieved in the process.

Step 6a: Slurry or Filtrate Batch Distillation

The slurry from Step 4 or Filtrate from step 5 is charged to a glass batch distillation provided with an impeller to keep the slurry in a suspended state. The glass vessel is immersed in a heater oil batch to provide the necessary energy input. The vapors from the batch distillation are condensed in a shell and tube condenser chiller with water or water/glycol mixture to condense the vapor. The distillation/condenser unit is operated at vacuum levels between 0.01 ton- to 100 torr. The slurry fed to the process is distilled and resultant condensate is clear water like liquid containing the required compounds that deliver the desired functionality based on formulation selected. The slurry is distilled until the slurry left over in the batch still gets to a highly viscous mass which can no longer be held in a state of suspension. The residence time for the batch ranges from 3 hours to 12 hours. The overall efficiency of condensate recovery varies from 40-60%.

Step 6b: Agitated Thin Film Evaporator (ATFE) or Wet Film Evaporator (WFE)

The slurry from step 4 is charged to an Agitated Thin Film Evaporator (ATFE). This method of evaporation is also sometimes referred to as Wet Film Evaporator (WFE).

The Agitated Thin film evaporator (ATFE) consists of two major assemblies—jacketed shell and a rotor assembly which rotates at high speed inside the shell. The feed enters evaporator at top, tangential to shell and gets distributed along the shell by the distributor. The rotor blades spread the feed evenly on the heated surface into a thin film and further agitate the film. Heating medium passing through the jacket evaporates the volatile component in feed. The vapor generated flow counter currently to feed and gets cleared in entrainment separator before leaving through vapor nozzle. The vapors are condensed in a shell and tube condenser where chilled water or water/glycol mixture. The system is operated under vacuum ranging from 0.01 torr to 100 torr. The solid slurry exits from the bottom of the unit in a solid powder form. The overall recovery of the condensate varies from 70% to 95%. The residence time in the ATFE unit varies from 1 second to 60 seconds.

Step 6c: Activated Carbon Treatment of Filtrate

The filtrate from Step 5 is passed through a column containing activated carbon with high specific surface area to remove colorants from herbal filtrate from Step 5. Phenolic compounds are the main contributor to the intense dark colour of the herbal filtrate from step 5. The color removal is accomplished with activated carbon with BET surface area of 500-1,700 sq metres per gram. The filtrate from the step 5 is passed through the activated column and the color containing compounds are removed from the filtrate causing a significant reduction of color of the filtrate. The resultant liquid is used for diabetes management, to treat carbohydrates to lower Glycemic Index and also provide low oil absorbing characteristics.

Step 6d: Ion Exchange Treatment of Filtrate

The filtrate from Step 5 is passed through an ion-exchange column containing polymers with high specific surface area and affinity to remove colorants from herbal filtrate from Step 5. The color removal is accomplished with anionic polymers such as microporous grade polystyrenic strong base type I anion exchanger having quarternary ammonium functional groups, non-ionic polydivinyl benzene adsorbant resins, styrene matrix and acrylic matrix resins with BET surface area of 500-1,200 sq metres per gram are typically used. The filtrate from the step 5 is passed through the ion exchange column and the color containing compounds are removed from the filtrate causing a significant reduction of color of the filtrate. The resultant liquid is used for diabetes management, to treat carbohydrates to lower Glycemic Index and also provide low oil absorbing characteristics. The ion exchange column is regenerated once the resins reach the absorption capacity at which point the ion exchange column is back flushed with a strong acid or base solution based on the ion exchange resin selected to regenerate the resin for reuse.

Step 7: Herbal Condensate Utility

The mixed, multi-component herbal condensate is produced from multiple herbs and spices and the efficacy ingredients that are evaporated and condensed are complex containing multiple components that deliver multiple mechanisms of action and functionality.

The herbal water condensate when used as a daily supplement is found to lower blood sugars as measured by Fasting Blood Glucose, Post Prandial blood Glucose, Glycated hemoglobin. The herbal waters are also found to lower lipids levels.

The fortified carbohydrates including fortified rice, whole wheat flour, refined wheat flour, rice flour, millet flours, urad flour, besan flour, potato or combinations of these flours when used in deep fried foods such as poori, chakli (or murukku), noodles, vada, potato chips, french fries, frying batters and other foods tend to absorb 10-50% less oil than using un-fortified flours.

EXAMPLES

The present invention is represented below by the help of representative examples. The examples do not limit the scope of the present invention. Mixed Herbs Formulation Herbs and spices were purchased and stored as per storage conditions specified above. Each of the ingredients purchased were ground as per grinding conditions listed in Table 2. The following two formulations: Formulation 1 summarized in Table 2 and covers Examples 1 to 13. Formulation 2 summarized in Table 3 covers Examples 2 to 4.

TABLE 1

Mixed Herbal Powder Formulation 1

| Common Name | Scientific Name | Part of the Plant Used | Formulation 2 |
|---|---|---|---|
| Coriander Seeds | *Coriandrum sativum* L. | Seeds | 1.0% |
| Star Anice | *Illicium verum* | Fruit | 1.0% |
| Turmeric | *Curcuma longa* | Root | 4.0% |
| Cumin | *Cuminum cyminum* | Seeds | 5.0% |
| Black Cumin | *Nigella sativa* | Seeds | 5.0% |
| Fenugreek | *Trigonella foenum-graecum* | Seeds | 5.0% |
| Black Pepper | *Piper nigrum* | Fruit | 6.0% |
| Clove | *Syzygium aromaticum* | Flower Buds | 3.5% |
| Ginger | *Zingiber officinale* | Root | 6.0% |
| Indian Gooseberry (Amla) | *Phyllanthus emblica* | Fruit | 7.0% |
| Black Plum (Black Jamun) | *Syzygium cumini* | Fruit & Seed | 15.0% |
| Cinnamon | *Cinnamomum verum* | Bark | 5.0% |
| Indian Senna | *Senna alexandrina* | Roots, Stem, Leaves, Flower | 28.0% |
| Guava | *Psidium guajava* | Leaves & Fruit | 2.5% |
| White Pepper | *Piper Nigrum* | Fruit | 1.5% |
| Ajwain | *Trachyspermum ammi* | Fruit | 2.0% |
| Fennel | *Foeniculum vulgare* | Fruit | 2.5% |
| Total | | | 100.0% |

TABLE 2

Mixed Herbal Powder Formulation 2

| Common Name | Scientific Name | Part of the Plant Used | Formulation 1 |
|---|---|---|---|
| Black Plum (Black Jamun) | *Syzygium cumini* | Fruit & Seed | 35.0% |
| Indian Gooseberry (Amla) | *Phyllanthus emblica* | Fruit | 12.0% |

TABLE 2-continued

| Mixed Herbal Powder Formulation 2 | | | |
| --- | --- | --- | --- |
| Common Name | Scientific Name | Part of the Plant Used | Formu- lation 1 |
| Black Pepper | *Piper nigrum* | Fruit | 10.0% |
| Fenugreek | *Trigonella foenum-graecum* | Seeds | 10.0% |
| Turmeric | *Curcuma longa* | Root | 10.0% |
| Cinnamon | *Cinnamomum verum* | Bark | 7.5% |
| Clove | *Syzygium aromaticum* | Flower Buds | 7.5% |
| Ginger | *Zingiber officinale* | Root | 7.5% |
| Total | | | 100.0% |

Example 1: Use of Herbal Extract Formulation 1 as an Adjunctive Supplement in Blood Glucose Management Mixed herbal powder Formulation 1 summarized in Table 1 was used in the test. 60 kg of this mixed herbal powder was dispersed in 240 litres of water. The slurry was kept in suspension with a motorized impeller for 12 hours.

The distillation equipment used in this example was agitated thin film evaporator or ATFE. ATFE consists of cylindrical, vertical body with heating jacket and a rotor inside of the shell which is equipped with rows and blades all over the length of the dryer. The hinged blades spread the wet feed product in a thin film over the heated wall. The turbulence increases as the product passes through the clearance before entering calming zone situated behind the blades as the heat will transfer from jacket to main shell under the smooth agitation water/solvent will evaporate and liquid will convert to slurry, to cake or to dry powder as it drops to the bottom of the unit. The vapors produced rise upward, counter-currently to the liquid and passed through Cyclone separator mounted of vapor outlet of ATFE. Further the vapors containing herbal ingredients are condensed in condenser. The system is operated under vacuum to facilitate boiling at lower temperatures.

The slurry was charged to the ATFE at a flow rate of 5 kg per minute. The ATFE used in this example consisted of a 1 sq m cylindrical surface area. The swiping blades rotated at 60 rpm and scraped the surface to form a thin film to facilitate rapid heat transfer and evaporation. The condenser surface area was 2.5 sq m. The condenser was water cooled where water circulating at 25 deg C. inlet and 27 deg c outlet temperature. The shell of the ATFE cylinder was circulated with ethylene glycol at 150 deg C. The ethylene glycol was heated with a diesel hot oil furnace which provided the energy source. The process at a vacuum of 25 mm Hg (or 25 torr) and 225 litres of the herbal concentrate was collected. The boiling point at this vacuum was 51 deg C. The residence time of the slurry in the ATFE was 7 seconds. Overall process yield from herbal water to herbal condensate was 90%. The herbal condensate was crystal clear and free of any color and did not have any residual taste of herbs or spices.

Herbal water condensate was used as an adjunctive supplement in blood glucose management in type 2 diabetics as the ingredients used in the formulation are well known to be effective in diabetics. A single centric, open-label study to evaluate the efficacy of Diabliss Diabetes Herbal Solution in Type-II Diabetes mellitus patients was undertaken. A total of ten type 2 diabetics were selected in the age group of 45 to 65 years of age with fasting blood glucose levels between 120 to 265 mg/dl. All subjects were provided with disclosures on the trial and consent was obtained prior to the initiation of the trail.

The duration of this study was 3 months (90-days). The subjects continued their standard medications and supplemented the medication with the herbal extract condensate. Each subject consumed 7.5 ml of the herbal extract at breakfast.

Figure 2:
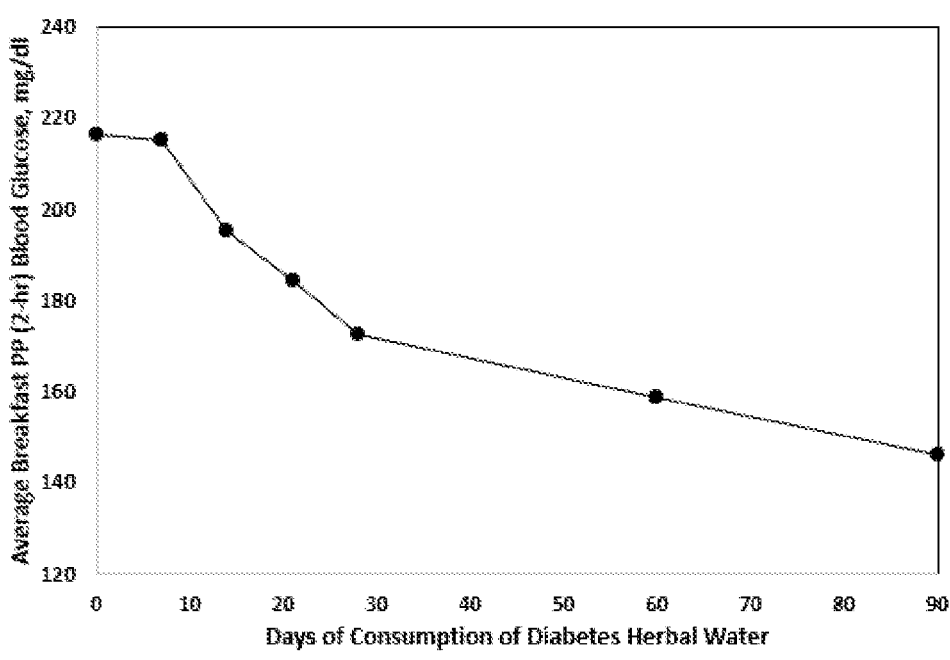
Figure 3:
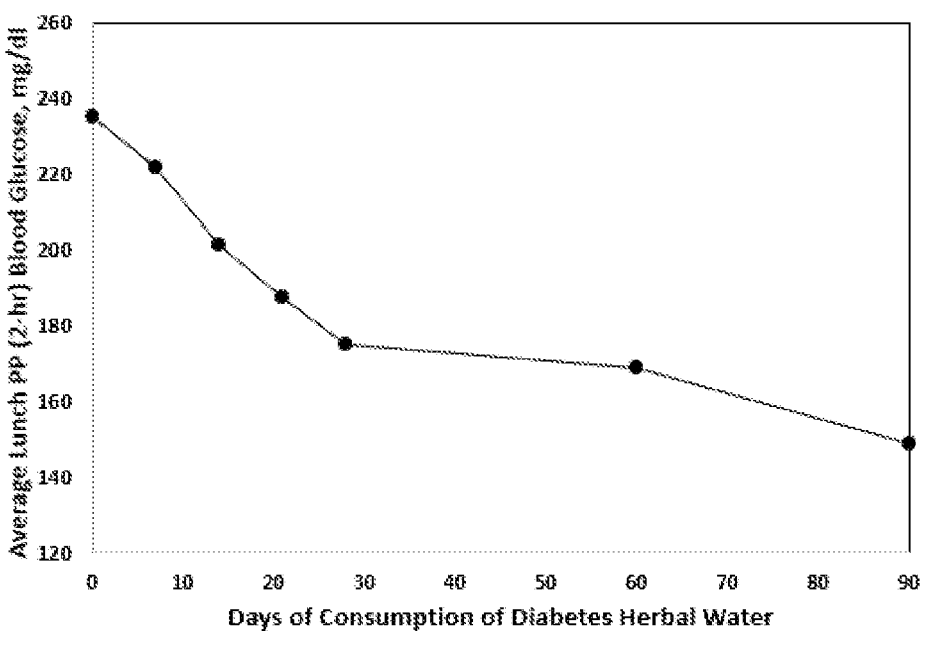

Fasting blood glucose (FBG), post prandial blood glucose (PPBG) 2 hours after breakfast, PPBG 2 hours after lunch were measured prior to start of the trial, i.e., Day 0, Day 7, Day 14, Day 21, Day 28, Day 60 and Day 90. Table 3 summarizes blood glucose parameters. FIGS. 1,2,3 summarizes average FBG, average PPBG 2 hours after breakfast and average PPBG 2 hours after lunch for all the subjects at the start of the trial and at days 7, 14, 21, 30, 60 and 90.

The data shows statistically significant reduction in FBG and PPBG. All ten subjects saw gradual and continuous reductions in fasting and post prandial blood glucose levels after breakfast and lunch. The efficacy which can be characterized by percent reduction in the blood glucose levels is very high. The effectiveness which is a measure of the percent of subjects indicates 100% of the subjects saw reduction in blood glucose parameters. Further the current herbal extract allows an easily consumable water format with good organoleptic properties in addition to good functional properties, making it an easy consumption of the herbal waters on a daily basis by diabetics.

TABLE 3

| Ten-subject Average Fasting, Post Prandial 2 hrs after breakfast & Post prandial 2 hours after lunch blood glucose data | | | | | | | |
| --- | --- | --- | --- | --- | --- | --- | --- |
| | Day | | | | | | |
| | 0 | 7 | 14 | 21 | 28 | 60 | 90 |
| Average Blood Glucose Parameters, mg/dl: | | | | | | | |
| Average Fasting, mg/dl | 171 | 162 | 154 | 140 | 135 | 120 | 112 |
| Average Breakfast Post Prandial (after 2 hrs), mg/dl | 217 | 215 | 195 | 184 | 173 | 159 | 146 |
| Average Lunch Post Prandial (after 2 hrs), mg/dl | 235 | 222 | 201 | 188 | 175 | 169 | 149 |
| Percent reduction in Average Blood Glucose Parameters vs. | | | | | | | |

TABLE 3-continued

| Ten-subject Average Fasting, Post Prandial 2 hrs after breakfast & Post prandial 2 hours after lunch blood glucose data | | | | | | | |
|---|---|---|---|---|---|---|---|
| | Day | | | | | | |
| | 0 | 7 | 14 | 21 | 28 | 60 | 90 |
| Baseline (Day 0): | | | | | | | |
| Average Fasting vs. Baseline, % reduction | | −5% | −10% | −18% | −21% | −30% | −35% |
| Average PP 2 hr Breakfast vs. Baseline, % reduction | | −1% | −10% | −15% | −20% | −27% | −32% |
| Average PP 2 hr Lunch vs. Baseline, % reduction | | −6% | −14% | −20% | −25% | −28% | −37% |

Example 2: Use of Herbal Extract Formulation 2 as an Adjunctive Supplement in Blood Glucose Management Mixed herbal powder Formulation 2 summarized in Table 2 was used in the test. 14 kg of this mixed herbal powder was dispersed in 56 litres of water. The slurry was kept in suspension with a motorized impeller for 12 hours. The resultant slurry was charged to a 100 litre glass batch distillation still along condenser with a 2.5 sq m condensing surface area. The condenser was water cooled where water circulating at 3 deg C. inlet and 5 deg c outlet temperature. The glass vessel was immersed in a 50/50 ethylene glycol batch and heat input to the ethylene glycol was provided by an electrical heating element which was set at 150 deg C. The process was operated for 5 hours at a vacuum of 0.1 mm Hg (0.1 torr) and 30 litres of the herbal concentrate was collected. The boiling point of the batch was 41 deg C. Overall process yield from herbal water to herbal condensate was 53.6%. The herbal condensate was crystal clear and free of any color.

Herbal extract condensate was used as an adjunctive supplement in blood glucose management in type 2 diabetics as the ingredients used in the formulation are well known to be effective in diabetics. A single centric, open-label study to evaluate the efficacy of herbal extract condensate in type 2 diabetes mellitus patients was undertaken. A total of 45 male and female type 2 diabetes mellitus patients selected with 35-55 years age group with fasting blood glucose levels between 150-200 mg/dL besides surviving with standard medication for clinical trial study. There were 21 male and 24 female subjects with an average age of 44 years. The procedures for these patients were reviewed and approved by the Institutional Ethical Committee for clinical trials. The trial was conducted in agreement with the International Conference on Harmonization (ICH) guidelines on Good Clinical Practice (GCP).

The duration of the study was 6 months (180-days). The subjects continued their standard medications and supplemented the medication with the herbal extract. Each subject consumed 7.5 ml of the herbal extract condensate mixed with 500 ml of water and consumed in equal proportions during breakfast, lunch and dinner. The testing consisted of four phases and the subjects, after phase 0 screening phase came in four time where comprehensive blood parameters were taken and analyzed. The following were the phases for the clinical trials analysis:

Phase 0—Screening Visit (Day −3 to Day 0)

Phase 1—Baseline Visit (Day 0)

Phase 2—Follow-up Visit (Day 1 to Day 30)

Phase 3—Follow-up Visit (Day 1 to Day 90)

Phase 4—End of Study Visit (day 180)

All the trials were conducted after obtaining consent from each of the subjects.

Table 4 tabulates key blood glucose parameters & lipids parameters. In the table, FBG=Fasting Blood Glucose in mg/dl PPBG=Post Prandial Blood Glucose (2 hours after meal) in mg/dl HbA1c=Glycated Hemoglobin or measure of 3-month average of blood glucose control as %

Lipids:

Total Cholesterol=Sum total of LDL, HDL & VLDL cholesterol in mg/dl

Triglycerides=Triglycerides in mg/dl

Data in table 4 shows reductions in all blood glucose and lipids parameters. Data indicates the reductions among men and women who participated in this study to be similar FIGS. 4, 5, 6 & 7 summarizes average FBG, PPBG, HbA1c and Total Cholesterol respectively during the course of the trial during the 180-day period.

The data shows statistically significant reduction in FBG, PPBG, HbA1c and lower lipids levels. 100% of the clinical trial participants showed reduction in FBG, PPBG, Total Cholesterol and Triglycerides. 97.8% of the participants or 44 of the 45 participants showed lowering of HbA1c. These findings indicate higher reductions in the various blood glucose parameters versus with the single component clinical studies which are discussed in Example 6. By combining multiple herbs diverse benefits are integrated into one product. Further the current herbal extract condensate allows an easily consumable water format with good organoleptic properties in addition to good functional properties, making it an easy consumption of the herbal waters on a daily basis by diabetics.

TABLE 4

| | FBG, mg/dl | PPBG, mg/dl | HbA1c, % | FBG, mg/dl | PPBG, mg/dl | HbA1c, % | FBG, mg/dl | PPBG, mg/dl | HbA1c, % |
|---|---|---|---|---|---|---|---|---|---|
| | | All Subjects | | | Male Subjects | | | Female Subjects | |
| Day 0 Average | 176 | 231 | 8.9 | 176.2 | 238.3 | 9.0 | 174.0 | 238.3 | 8.8 |
| Day 30 Average | 155 | 204 | | 153.4 | 206.2 | | 152.8 | 206.2 | |
| Day 90 Average | 140 | 180 | 7.4 | 138.8 | 179.9 | 7.4 | 138.6 | 179.9 | 7.3 |
| Day 180 Average | 91 | 132 | 7.1 | 90.7 | 132.7 | 7.2 | 91.2 | 132.7 | 7.1 |

Clinical Trial Data - Blood Glucose and Lipids Parameters

Average % Reduction vs. Baseline

| | FBG | PPBG | HbA1c | FBG | PPBG | HbA1c | FBG | PPBG | HbA1c |
|---|---|---|---|---|---|---|---|---|---|
| | | All Subjects | | | Male Subjects | | | Female Subjects | |
| | Day 30 vs Day 0 | Day 90 vs Day 0 | Day 180 vs Day 0 | Day 30 vs Day 0 | Day 90 vs Day 0 | Day 180 vs Day 0 | Day 30 vs Day 0 | Day 90 vs Day 0 | Day 180 vs Day 0 |
| FBS | −12% | −21% | −48% | −12.9% | −21.3% | −48.6% | −12.2% | −20.4% | −47.6% |
| PPG | −12% | −22% | −43% | −13.5% | −24.5% | −44.3% | −13.5% | −24.5% | −44.3% |
| HbA1c | | −17% | −20% | | −17.9% | −20.1% | | −17.1% | −20.1% |

Lipids Level

| | Avg Total Cholesterol, mg/dl | Triglycerides, Avg. mg/dl |
|---|---|---|
| Day 0 | 173 | 99 |
| Day 180 | 151 | 83 |
| Delta vs. Baseline | 13.0% | −15.9% |

Example 3: Low Oil Absorbing Properties of Herbal Fortified Grains and Legumes Herbal extract described in more detail in example 2 was uniformly mixed with grains and legumes as shown in Table 5. These materials were then allowed to stand for 4 hours to allow absorption of the herbal extract into the grains and legumes. The grains and legumes were then dried in an over set at 50 deg C. to their original starting weight. Each of the grains and legumes were then ground in a laboratory hammer mill and used in various deep-frying applications.

In table 5 the details of the Staple used, the Savory or Food Product, formulation details of various components used, type of oil used in deep frying, the amount of herbal extract used in treatment of the grains and legumes in terms of ml of herbal extract per kg of the grain and legume, frying temperature of the oil used in the electrical fryer, the weight of the oil charged to fryer, weight of the oil left over at the end of the test is tabulated. From this, the reduction in oil absorption for the particular savory or food made without herbal extract (control) is compared against the same savory made with herbal extract treated flours as summarized in the Table 5.

Data on oil absorption shows the impact of herbal treatment in lowering the oil absorbed in these deep-fried foods. As oil contains much higher calorific values, this allows savories and foods to be produced with lower calorific values.

FIG. 8 is a cross sectional photograph of the cross section of millet murukku from control samples versus millet murukku from herbal treatment. The photograph shows lower penetration of the oil across the cross section for herbal treated product resulting in lower oil absorption as summarized in Table 5. As oil contains much higher calorific value, the current invention allows savories and foods to be produced with lower calorific inputs and therefore can help with weight management which is also an important aspect of lowering risk factors for diabetics.

TABLE 5

Oil absorption of various foods with and without treatment with Formulation 1 herbal extract in deep frying

| Savory or Food Product | Component 1, kg | Component 2, Kg | Component 3, Kg | Oil Type | Herbal Extract Used in Treatment, ml/kg | Frying Temp, Deg C. | oil charged to fryer, kg | Oil @ end of frying, kg | Oil absorbed, g | Oil Absorption Reduction, % |
|---|---|---|---|---|---|---|---|---|---|---|
| | Wheat | | Water | | | | | | | |
| Wheat Poori - Control | 1 | | 0.6 | Sunflower | | 220 | 3000.0 | 2784.5 | 215.50 | |
| Wheat Poori - Herbal Treatment | 1 | | 0.6 | Sunflower | 40 | 220 | 3000.0 | 2874.5 | 125.5 | −41.8% |
| | Wheat | Fox Tail Millet | Water | | | | | | | |
| Millet Poori - Control | 0.25 | 0.25 | 0.6 | Sunflower | | 220 | 1000 | 835 | 165 | |
| Millet Poori - Herbal Treatment | 0.25 | 0.25 | 0.6 | Sunflower | 40 | 220 | 1000 | 890.5 | 109.5 | −33.6% |
| | Maida | | Water | | | | | | | |
| Maida Poori - Control | 0.1 | | 0.05 | | | | 250.0 | 160.5 | 89.50 | |
| Maida Poori - Herbal Treatment | 0.1 | | 0.05 | | 40 | | 250.0 | 175 | 75.0 | −16.2% |
| | Wheat | | Water | | | | | | | |

TABLE 5-continued

Oil absorption of various foods with and without treatment with Formulation 1 herbal extract in deep frying

| Savory or Food Product | Component 1, kg | Component 2, Kg | Component 3, Kg | Oil Type | Herbal Extract Used in Treatment, ml/kg | Frying Temp, Deg C. | oil charged to fryer, kg | Oil @ end of frying, kg | Oil absorbed, g | Oil Absorption Reduction, % |
|---|---|---|---|---|---|---|---|---|---|---|
| Noodles - Control | 0.5 | | 0.5 | Sunflower | | 220 | 3000.0 | 2646 | 354.0 | |
| Noodles - Herbal Treatment | 0.5 | | 0.5 | Sunflower | 40 | 220 | 3000.0 | 2750 | 250.0 | −29.4% |
| | Rice Flour | | Water | | | | | | | |
| Murukku - Control | 3.0 | | 1.5 | Sunflower | | 180 | 5000.0 | 3939.0 | 1061.0 | |
| Murukku - Herbal Treatment | 3.0 | | 1.5 | Sunflower | 40 | 180 | 5000.0 | 4213.5 | 786.5 | −25.9% |
| | Rice Flour | Fox Tail Millet Flour | Water | | | | | | | |
| Fox Tail Millet Murukku - Control | 0.50 | 0.50 | 0.5 | Sunflower | | 180 | 3000.0 | 2675.5 | 324.5 | |
| Fox Tail Millet Murukku - Herbal Treatment | 0.50 | 0.50 | 0.5 | Sunflower | 60 | 180 | 3000.0 | 2762 | 238 | −26.7% |
| | Urad Dhal | | Water | | | | | | | |
| Vada - Control | 0.25 | | 0.41 | Sunflower | | 180 | 1000.00 | 876 | 124.0 | |
| Vada - Herbal Treatment | 0.25 | | 0.41 | Sunflower | 70 | 180 | 1000.00 | 896 | 104.0 | −16.1% |
| | Besan Flour | Rice Flour | Water | | | | | | | |
| Ribbon Pakoda - Control | 0.67 | 0.33 | 0.6 | Sunflower | | 190 | 3.00 | 2.753 | 247 | |
| Ribbon Pakoda - Herbal Treatment | 0.67 | 0.33 | 0.6 | Sunflower | 60 | 190 | 3.00 | 2.793 | 206.5 | −16.4% |

Example 4— Low Oil Absorption of Savories with Formulation 1

Herbal extract described in more detail in example 1 was uniformly mixed with the following grains and legumes at the rate shown in Table 6.

These materials were then allowed to stand for 4 hours to allow absorption of the herbal extract into the grains and legumes. The grains and legumes were then dried in an over set at 50 deg C. to their original starting weight. Each of the grains and legumes were then ground in a laboratory hammer mill and used in various deep-frying applications.

In Table 6 the details of the staple used, the savory or food product, formulation details of various components used, type of oil used in deep frying, the amount of herbal extract used in treatment of the grains in terms of ml of herbal extract per kg of the grain and legume, frying temperature of the oil used in the electrical fryer, the weight of the oil charged to fryer, weight of the oil left over at the end of the test is tabulated. From this, the reduction in oil absorption for the particular savory or food made without herbal extract (control) is compared against the same savory made with herbal extract treated flours as summarized in the Table 6.

Data on oil absorption shows the impact of herbal treatment in lowering the oil absorbed in these deep-fried foods with formulation 1. As oil contains much higher calorific value, the current invention allows savories and foods to be produced with lower calorific inputs and therefore can help with weight management which is also an important aspect of lowering risk factors for diabetics.

TABLE 6

Oil absorption of various foods with and without herbal; treatment in deep frying applications with formulation 2

| Test | Staple | Savory or Food Product | Component 1, kg | Component 2, Kg | Component 3, Kg | Oil Type |
|---|---|---|---|---|---|---|
| | | | Wheat | | Water | |
| 1 | Wheat | Wheat Poori - Control | 1 | | 0.6 | Sunflower |
| 2 | Wheat | Wheat Poori - Herbal Treatment | 1 | | 0.6 | Sunflower |
| | | | Rice Flour | | Water | |
| 3 | Rice | Murukku - Control | 3.0 | | 1.5 | Sunflower |
| 4 | Rice | Murukku - Herbal Treatment | 3.0 | | 1.5 | Sunflower |
| | | | Rice Flour | Fox Tail Millet Flour | Water | |

TABLE 6-continued

| | | Oil absorption of various foods with and without herbal; treatment in deep frying applications with formulation 2 | | | | |
|---|---|---|---|---|---|---|
| 5 | Rice/Fox Tail Millet | Fox Tail Millet Murukku - Control | 0.50 | 0.50 | 0.5 | Sunflower |
| 6 | Rice/Fox Tail Millet | Fox Tail Millet Murukku - Herbal Treatment | 0.50 | 0.50 | 0.5 | Sunflower |

| Test | Herbal Extract Used in Treatment, ml/kg | Frying Temp, Deg C. | Oil charged to fryer, kg | Oil @ end of frying, kg | Oil absorbed, g | Oil Absorption Reduction, % |
|---|---|---|---|---|---|---|
| 1 | | 220 | 3000.0 | 2775.0 | 225.00 | |
| 2 | 40 | 220 | 3000.0 | 2850.0 | 150.00 | −33.3% |
| 3 | | 180 | 3000.0 | 2653.5 | 346.5 | |
| 4 | 40 | 180 | 3000.0 | 2734.5 | 265.5 | −23.4% |
| 5 | | 180 | 3000 | 2675.5 | 324.5 | |
| 6 | 60 | 180 | 3000 | 2762 | 238 | −26.7% |

Example 5: Increased Efficacy and Effectiveness of Use of Herbs & Spices with Formulations 1 and 2 Versus Consuming Single Herbs and Spices in the Native Form Table 7 summarizes blood glucose parameters (FBG, PPBG, HbA1c) data from Examples 1 and 2 to compare the impact of the current process and formulations in terms of efficacy versus published clinical trial data from consumption of single herbs and spices in their native form.

1. Example 1 blood parameters vs. single herbs reported clinical data: By day 90, FBG reduction was 35% reduction in FBG after consuming 7.5 ml of herbal extract condensate admixed with 500 ml of water. The 7.5 ml of herbal extract condensate was produced from 2.2 grams of the herbal mixture summarized in Table 1. This compares with in FBG 30% reduction by consuming 10 g per day of Black Jamun fruit and 12.7% reduction by consuming 2 g per day of Ginger for 90 days. In comparison, 19.2% reduction in FBG was noted after 6 months of consuming 30 g/day of Indian gooseberry or Amla.

2. Example 2 blood parameters vs. single herbs reported clinical data: The herbal extract condensate summarized in Example 2 achieved 17% reduction in HbA1c versus 6.73% reduction by consuming 10 g of black jamun daily after 90 days while black jamun achieved higher fasting and the same PPBG reduction as the herbal condensate extract. Today, medical professionals are increasingly relying of HbA1c to gauge the response of diabetics as it represents the long-term average of blood glucose control. Further, as the herbal extract condensate was tested for 180 days, FBG and PPBG reductions of 48% and 43% respectively were recorded by 180 days. So, day 90 HbA1c was 2.52 times lower using 7.5 ml of herbal extract condensate produced with 2.5 g Comparing against consumption of 100 g of Fenugreek daily achieved HbA1c reduction of 9.87% versus herbal extract condensate from Example 2 achieving 17% reduction in HbA1c Comparing against consumption of 30 g of Amla daily achieved HbA1c reduction of 19.2% versus herbal extract condensate achieving 21% reduction in HbA1c in 180 days. Amla clinical data reported FBG reduction of 17.8% versus 48% reduction with herbal water condensate described in example 2.

Consuming large quantities of these ingredients daily poses a serious problem as organoleptic properties and the form in which these materials have to be consumed makes it difficult for diabetics to adhere to such a regimen. On the other hand, the embodiments described in this invention delivers higher results in terms of HbA1c, FBG, PPBG and lipids levels in an easy to consume format with enhanced organoleptic properties.

TABLE 7

| | Comparison of HbA1c, FBG, PPBG of formulations from current invention versus single herbs and spices clinical data reported in literature | | | | |
|---|---|---|---|---|---|
| Examples from Current Invention/ Individual Herbs Consumed | Daily Dosage Administered | HbA1c | | Fasting Blood Glucose | Post Prandial Blood Glucose |
| Example 1 | 7.5 ml (produced from 2.2 g of mixed herbal powder) | | | Day 30: 18% reduction Day 60: 30% reduction Day 90: 35% reduction | PPBG, 2 hrs after Breakfast: Day 28: 20% reduction Day 60: 27% reduction Day 90: 32% reduction PPBG, 2 hrs after lunch: Day 28: 25% reduction Day 60: 28% reduction Day 90: 27% reduction |

TABLE 7-continued

| | | | | |
|---|---|---|---|---|
| Comparison of HbA1c, FBG, PPBG of formulations from current invention versus single herbs and spices clinical data reported in literature | | | | |
| Examples from Current Invention/ Individual Herbs Consumed | Daily Dosage Administered | HbA1c | Fasting Blood Glucose | Post Prandial Blood Glucose |
| Example 2 | 7.5 ml (produced from 2.3 g of mixed herbal powder) | Day 180: 20% reduction Day 90: 17% reduction | Day 30: 12% reduction Day 90: 21% reduction Day 180: 48% reduction | PPBG, 2 hrs after Breakfast: Day 30: 12% reduction Day 90: 22% reduction Day 180: 43% reduction |
| Black Jamun Fruit (Reference 1) | 10 g/day | Day 90: 6.73% reduction | Day 90: 30% reduction | Day 90: 22% reduction |
| Fenugreek Powder (Reference 2) | 100 g/day total | Day 90: 9.87% reduction | Not Reported | Not Reported |
| Ginger (Reference 3) | 2 g/day | Day 90: 10.4% reduction | 90 days: 12.7% reduction | Not Reported |
| Indian Gooseberry (Amla) (Reference 4) | 30 g/day | Day 90: 10.5% reduction | 6 months: 19.2% reduction | 6 months: 17.8% reduction |
| Cinnamon (Reference 5) | 1 g per day | Day 90: 9.8% reduction | Not Reported | Not Reported |

References cited in Table 7:
1. Sidana S, Singh V B, Meena B L, Beniwal S, Singh K, Kumar D, et al. Effect of *Syzygium cumini* (jamun) seed powder on glycemic control: A double-blind randomized controlled trial. J Med Soc 2017; 31:185-9.
2. Ansari R, Ansari S, Effectiveness of Fenugreek for Lowering Hemoglobin (HbA1c) in Patients with Self-Management of Type 2 Diabetes: A Randomized Controlled Trial, Open Peer Reviewed Chapter, Intech Open, www.intechopen.com, September 2011
3. Khandouze N, Shidfar F, Rajeb A, Rahideh T, Hosseini P, Taheri M M, The Effects of Ginger on Fasting Blood Sugar, Hemoglobin A1c, Apolipoprotein B, Apolipoprotein A-I and Malondialdehyde in Type 2 Diabetic Patients Iranian Journal of Pharmaceutical Research (2015), 14 (1): 131-140
4. Santhi Sri K V, Jalaja Kumari D, Sivanarayana G, Effect of Amla, an approach towards the control of Diabetes mellitus, Int.J.Curr.Microbiol.App.Sci (2013) 2(9): 103-108
5. Crawford P, Effectiveness of Cinnamon for Lowering Hemoglobin A1C in Patients with Type 2 Diabetes: A Randomized, Controlled Trial, J Am Board Fam Med: first published as 10.3122/j abfm.2009.05.080093

Example 6: Herbal Extract with Improved Organoleptic Properties Produced with Activated Carbon Treatment Mixed herbal powder Formulation 2 summarized in Table 2 was used in the test.

5 kg of this mixed herbal powder was dispersed in 20 litres of water. The slurry was kept in suspension with a motorized impeller for 12 hours. The slurry was then filtered in a plate and frame filter press at a pressure of 5 kg per sq cm. 11 litres of filtrate was collected. The filtrate was dark brown in color.

10 litres of the filtrate was then charged to a 20 litre glass agitated vessel and immersed in an oil bath. The temperature of the slurry was maintained at 55 deg C. Upon reaching this temperature, 250 grams of activated carbon with BET surface area of 1,000 square meters per gram was charged to the vessel agitated with an impeller at 200 rpm. After 40 minutes of stirring the slurry containing activated carbon and the herbal filtrate, the slurry was filtered in a Buchner funnel with a Whatman Filter Paper Grade 6 using a vacuum pump to increase filtration rate.

The filtrate collected had substantially reduced coloration. The taste of the filtrate also had much reduced residual taste when compared with the filtrate prior to activated carbon treatment.

Example 7: Herbal Extract with Improved Organoleptic Properties Produced with Ion Exchange Treatment Mixed herbal powder Formulation 1 summarized in Table 1 was used in the test.

5 kg of this mixed herbal powder was dispersed in 20 litres of water. The slurry was kept in suspension with a motorized impeller for 12 hours. The slurry was then filtered in a plate and frame filter press at a pressure of 5 kg per sq cm. 10.8 litres of filtrate was collected. The filtrate was dark brown in color. The filtrate was maintained at 50 deg C. and used in the ion exchange treatment process.

A 2 inch diameter and one meter long boro silicate glass column fitted with a stainless steel mesh at the bottom and a valve to regulate flow was changed with a microporous grade polystyrenic strong base type I resin having quaternary ammonium functional groups was charged o the ion exchange resin which was filled to 60 cm level in the glass ion exchange column. The filtered herbal water was pumped at a rate to 100 ml per minute with a syringe pump from the top of the column. The filtrate collected after passing through the ion exchange column.

The filtrate collected had the color of water and colour of the herbal water free from any residual color of the herbal extract. The taste of the filtrate also had much reduced residual taste when compared with the filtrate prior to activated carbon treatment.

Although the invention has been described with reference to specific embodiments, this description is not meant to be construed in a limiting sense. Various modifications of the disclosed embodiments, as well as alternate embodiments of the invention, will become apparent to persons skilled in the art upon reference to the description of the invention. It is therefore, contemplated that such modifications can be made without departing from the spirit or scope of the present invention as defined.

We claim:

1. A method for manufacturing a formulation of natural products comprising herbs, plants and/or spices and/or part thereof, with enhanced functional and organoleptic properties, said method comprising:

drying herbs and/or spices to achieve a moisture content of 5% to 25%, wherein the herbs and/or spices are selected from *Coriandrum sativum* L., *Illicium verum, Curcuma longa, Cuminum cyminum, Nigella sativa, Trigonella foenumgraecum, Piper nigrum, Syzygium aromaticum, Zingiber officinale, Phyllanthus emblica, Syzygium cumini, Cinnamomum verum, Senna alexandrina; Psidium guajava, Trachyspermum ammi*, or *Foeniculum vulgare.* grinding the herbs and/or spices to a resultant powder having a particle size of about 30 microns to about 300 microns;

homogenizing the resultant powder mixture with water into a slurry, by dissolving the powder mixture in water, followed by keeping it in a jacketed stirred tank for about 4 to about 16 hours at a temperature of 25° C. to 60° C. to form a slurry; and distilling or filtering the slurry selected from:

(i) distilling of the slurry and collecting a condensate therefrom; or (ii) filtering the slurry under pressure to obtain a filtrate and distilling the filtrate and collecting the condensate wherein distilling the filtrate and/or distilling the remaining slurry is performed in vacuum between 0.01 torr to 300 torr, and removing color and taste causing compounds to obtain the formulation of natural products.

2. The method as claimed in claim 1, wherein the grinding is by hammer mill or commercial food shredder pulveriser.

3. The method as claimed in claim 2, wherein the hammer mill is operated between 1500 RPM y 2000 RPM.

4. The method as claimed in claim 1, wherein the filtrate is subjected to either:

contacting the filtrate with activated carbon with a BET surface area of 500-1,700 sq metres per gram for a period of 30-60 minutes at a temperature of 35-65 deg C, to obtain the formulation of natural products; or contacting the filtrate in an ion-exchange column with anionic polymers selected from the group consisting of microporous grade polystyrenic strong base type I anion exchanger having quarternary ammonium functional groups, non-ionic polydivinyl benzene adsorbant resins, and styrene matrix and acrylic matrix resins with BET surface area of 500-1,200 sq metres per gram; and removing color and taste causing compounds after contact with the activated carbon or the anionic polymers to obtain the formulation of natural products.

5. The method as claimed in claim 1, wherein distilling the filtrate is performed in a rotary evaporator immersed in a heated water bath or a water and glycol bath.

6. The method as claimed in claim 5, wherein the evaporator is rotated at 40-70 rpm, and optionally fitted with a condenser cooled with chilled water or a water and glycol mixture.

7. The method as claimed in claim 1, wherein distilling the remaining slurry is by glass batch distillation.

8. The method as claimed in claim 7, wherein the glass batch distillation apparatus comprises an impeller and is immersed in a heated oil batch or is a shell and tube condenser, which is chilled with water or a water and glycol mixture.

9. The method as claimed in claim 7, wherein the glass batch distillation is operated at vacuum levels between 0.01 torr to 100 torr with a residence time in a range of 3 hours to 12 hours.

10. The method as claimed in claim 1, wherein the distillation of the slurry is carried out by charging the slurry to an Agitated Thin Film Evaporator (ATFE) or Wet Film Evaporator (WFE).

11. The method as claimed in claim 10, wherein charging the slurry is performed under vacuum ranging from 0.01 torr to 100 torr for a residence time ranging from 1 second to 60 seconds.

* * * * *